US00RE38723E

(19) United States
(12) Reissued Patent
Mao et al.

(10) Patent Number: US RE38,723 E
(45) Date of Reissued Patent: Apr. 12, 2005

(54) HALOALKYL DERIVATIVES OF REPORTER MOLECULES USED TO ANALYZE METABOLIC ACTIVITY IN CELLS

(75) Inventors: Fei Mao, Eugene, OR (US); Ram Sabnis, Sacramento, CA (US); John Naleway, Eugene, OR (US); Nels Olson, Homer, AK (US); Richard P. Haugland, Eugene, OR (US)

(73) Assignee: Molecular Probes, Inc., Eugene, OR (US)

(21) Appl. No.: 08/910,090

(22) Filed: Aug. 12, 1997

Related U.S. Patent Documents

Reissue of:
(64) Patent No.: 5,576,424
Issued: Nov. 19, 1996
Appl. No.: 08/336,285
Filed: Nov. 8, 1994

U.S. Applications:
(63) Continuation-in-part of application No. 08/026,633, filed on Mar. 5, 1993, now Pat. No. 5,362,628, which is a continuation of application No. 07/749,256, filed on Aug. 23, 1991, now abandoned.

(51) Int. Cl.[7] ..... C07H 17/00; C07D 309/00
(52) U.S. Cl. ..... 536/17.9; 536/4.1; 536/18.1; 549/356; 549/382
(58) Field of Search ..... 536/11.9, 4.1, 536/18.1, 17.9; 549/356, 382

(56) References Cited

U.S. PATENT DOCUMENTS

| | | | | |
|---|---|---|---|---|
| 3,808,232 A | * | 4/1974 | Hardt et al. | |
| 4,557,862 A | * | 12/1985 | Mangel et al. | 549/227 |
| 4,640,893 A | * | 2/1987 | Mangel et al. | 435/23 |
| 4,777,269 A | * | 10/1988 | Scheper et al. | 549/288 |
| 4,810,636 A | * | 3/1989 | Corey | 435/17 |
| 4,812,409 A | * | 3/1989 | Babb et al. | 435/7 |
| 5,070,012 A | * | 12/1991 | Nolan et al. | 435/6 |
| 5,110,725 A | * | 5/1992 | Marrone et al. | 435/11 |
| 5,208,148 A | * | 5/1993 | Haugland et al. | 435/14 |
| 5,242,805 A | * | 9/1993 | Naleway et al. | 435/18 |
| 5,362,628 A | * | 11/1994 | Haughland et al. | 435/18 |

OTHER PUBLICATIONS

Poot, et al. Cytometry 12, 1984 (1991).*
Gossrau, Histochem. J. 17, 737 (1985).*
Nakai, et al. J. Biol. Chem. 267, 19503 (1992).*
Mantle, et al. Biochem. Soc. Transactions 18, 175 (1990).*
Melamed, et al. Flow Cytometry and Sorting (2nd ed. 1990).*
Rice et al., Cancer Research 46, 6105 (1986).*
Shapiro, Practical Flow Cytometry (1985).*
Checa, et al., Analyt. Biochem. 190, 212 (1990).*
Kanaoka, et al., Chem. Pharm. Bull. 25, 603 (1977).*
Yoshimoto et al., Biochim. Biophys. Acta, 569, 184 (1979).*
Pierzchala, Biochem. J., 183, 555 (1979).*
Nolan, et al., Proc. Natl. Acad. Sci. USA 85, 2603, (1988).*
Grant & Matsumura, Insect Biochem 18 (6), 615 (1988).*

* cited by examiner

*Primary Examiner*—Elli Peselev
(74) *Attorney, Agent, or Firm*—Allegra Helfenstein; Anton Skaugset

(57) ABSTRACT

The subject invention provides substrates useful for analyzing the metabolic activity in cells by improving the retention of a detectable reporter molecule only in intact cells where a particular enzyme is present. In particular, improved retention results from a two part process involving conjugation of haloalkyl-substituted derivatives of a reporter molecule with intracellular cysteine-containing peptides while unblocking the reporter molecule. The substrates have the form

XR-SPACER-REPORTER-BLOCK wherein -BLOCK is a group selected to be removable by action of a specific analyte, to give REPORTER spectral properties different from those of the substrate, -REPORTER- is a molecule that, when no longer bound to BLOCK by a BLOCK-REPORTER bond, has spectral properties different from those of the substrate, -SPACER- is a covalent linkage, and XR- is a haloalkyl moiety that can covalently react with an intracellular thiol (Z-S-H) to form a thioether conjugate (Z-S-R).

After the substrate enters the cells, the analyte removes BLOCK to make REPORTER detectable by the change in spectral properties, and the haloalkyl XR reacts with the intracellular thiol to form the thioether conjugate inside the cells, which is well-retained in the cells.

25 Claims, 1 Drawing Sheet

HALOALKYL DERIVATIVES OF REPORTER MOLECULES USED TO ANALYZE METABOLIC ACTIVITY IN CELLS

Matter enclosed in heavy brackets [ ] appears in the original patent but forms no part of this reissue specification; matter printed in italics indicates the additions made by reissue.

This application is a continuation-in-part of application Ser. No. 08/026,633 filed Mar. 5, 1993, now U.S. Pat. No. 5,362,628, which is itself a continuation of application Ser. No. 07/749,256 filed Aug. 23, 1991, now abandoned.

This invention was made with Government support under grant no. GM 38987 awarded by the National Institutes of Health. The Government has certain rights in this invention.

FIELD OF THE INVENTION

The subject invention provides fluorogenic substrates for analyzing the metabolic activity in cells by improving the retention of a detectable reporter molecule only in intact cells where a particular enzyme is present. In particular, improved retention results from conjugation of haloalkyl-substituted derivatives of a reporter molecule with intracellular cysteine-containing peptides, while a detectable signal is provided by unblocking the reporter molecule.

BACKGROUND TO THE INVENTION

The presence and activity of enzymes can be used to determine the health and metabolic state of a cell. Enzymes are also markers for the cell type since the occurrence and activity of certain enzymes is frequently characteristic of a particular cell. For instance, the activity of certain enzymes can often be used to distinguish cells of bacterial, plant or animal origin. Enzymatic activity and integrity of the cell membrane is one of the criteria for cell viability.

Detection of the presence and activity of enzymes has been facilitated by the development of chromogenic or fluorogenic substrates that are converted by chemical action of the enzyme to a reporter molecule whose optical properties can be measured. Principal among the new reporter molecules have been fluorescent dyes. In many cases the high sensitivity of fluorescence detection permits measurements in living single cells with high spatial and temporal resolution that are not possible with dyes that are not fluorescent.

Unfortunately, many reporter dyes formed by action of intracellular enzymes on synthetic enzyme substrates rapidly leak from the cells, making qualitative and quantitative assays of cellular enzymatic activity difficult. Accurate measurement of enzymatic presence or activity in a single cell requires that the detectable reporter molecule is retained by the cell for the period required for its measurement. Furthermore, it is strongly preferred that the measurement can be made under physiological conditions and, if desired, in living tissue or cells.

An example where these properties are especially required is the use of foreign genes that code for enzymes as markers in cells. For instance, bacterial genes that code for production of β-galactosidase (lacZ) or β-glucuronidase (GUS) have been incorporated [(transletted)] (*transfected*) into plant and animal cells that do not ordinarily contain this activity. To determine the success of the incorporation, to sort and clone the [transletted] *transfected* cells, and to measure the effect of certain promoter genes that are simultaneously incorporated with the marker gene requires both that the reporter molecule formed by action of the enzyme on the substrate is retained in the single cell, and that its retention measures the level of enzymatic activity in the cell. The analysis and sorting of successfully cloned cells can be performed by flow cytometry if suitable probes are available that are retained inside the cell sufficiently long for the analysis to be completed.

A number of synthetic enzyme substrates have been used to determine the activity of enzymes in extracts of cells, in solution, or in living cells. Most of these substrates have been based on fluorescent reporter dyes such as 7-hydroxy-4-methylcoumarin (β-methylumbelliferone), 7-amino-4-methylcoumarin, 4-methoxy-2-naphthylamine, fluorescein, resorufin, rhodamine 110 or various derivatives of α- and β-naphthol. Quantitative detection of enzymatic activity in single, living cells under physiological conditions, whether intrinsic to the cell or incorporated by genetic manipulation, has been difficult because the reporter molecules formed by the enzymatic reaction of substrates based on the above fluorophores have been poorly retained in cells.

Certain substrates have been described for the histochemical localization of protease enzymes in cultured cells, that require addition of a second reagent to develop a weakly [fluorescenct] *fluorescent* product subsequent to the enzymatic reaction by Gossrau, Cytochemistry of Membrane Protease, HISTOCHEM. J. 17, 737 (1985). The requirement of a second reagent complicates the quantitative aspects of the measurements and makes the Gossrau procedure less desirable for use in applications that are highly automated.

Use [offluorescein] *of fluorescein* digalactoside (FDG) in an automated procedure to sort single lacZ-positive transfected cells has been described by Nolan et al., MONITORING OF CELLS AND TRANS-ACTING TRANSCRIPTION ELEMENTS, U.S. Pat. No. 5,070,012 (1991). Cells were loaded with this relatively impermeant substrate by hypoosmotic shock, then the cells were cooled to below 5° C. Although this permitted sorting of the cells at a supercooled temperature where the competition between the enzyme turnover rate and the leakage rate permitted retention of a portion of the fluorescent dye, it is not effective under physiological conditions. The leakage rate of potential alternative probes for monitoring lacZ or GUS gene fusion such as the resorufin formed by hydrolysis of resorufin galactoside and β-methylumbelliferone formed by hydrolysis of β-methylumbelliferyl glucuronide tends to be even faster.

Lipophilic derivatives of fluorescein and resorufin have been described in LIPOPHILIC FLUORESCENT GLYCOSIDASE SUBSTRATES (U.S. Pat. No. 5,208,148 to Haugland et al. (1993)) and LONG WAVELENGTH LIPOPHILIC FLUOROGENIC GLYCOSIDASE SUBSTRATES (U.S. Pat. No. 5,242,805 to Naleway et al. (1993)), where retention is enhanced by the addition of a lipophilic residue and can be used under physiological conditions. These substrates can be used with automated procedures but are not effective where the fluorescent label needs to be retained inside cells to which a fixative has been applied.

There is a need for a method for analyzing metabolic activity in cells under physiological conditions, using a substrate that yields fluorescence or absorbance detectable products that are retained in the cells for the time period required to accomplish relevant analysis. The fluorescence or absorbance should be detectable inside fixed cells as well as living cells and be distinct from background fluorescence or absorbance.

Glutathione transferase is known to catalyze the reaction of a wide variety of alkylating and arylating reagents with glutathione (Mantle, et al., Glutathione S-transferases, BIOCHEM. SOC. TRANSACTIONS, 18, 175 (1990)). This is an important process for detoxification of pollutants and dangerous chemicals by cells. The enzyme is ubiquitous, being found in both plant and animal cells. Free glutathione levels in most normal cells are relatively high (up to >1 mM).

A number of haloalkylated fluorescent reagents have been previously described for use in estimating the level of intracellular thiols in cells. Monochlorobimane is a chloroalkylated fluorescent reagent that has been used to measure glutathione levels in single cells by flow cytometry in a reaction that is catalyzed by glutathione transferase (Rice, et al., Quantitative Analysis of Cellular Glutathione by Flow Cytometry Utilizing Monochlorobimane: Some Applications to Radiation and Drug Resistance in Vitro and in Vivo, CANCER RESEARCH 46, 6105 (1986)). Monobromobimane is a reagent with similar utilizing however it is less selective for intracellular thiols than is monochlorobimane (Fernández-Checa, et al., The Use of Monochlorobimane to Determine Hepatic GSH Levels and Synthesis, ANALYT. BIOCHEM. 190, 212 (1990)). The use of chloromethylfluorescein diacetate (CMFDA) and chloromethyleosin diacetate (CMEDA) has previously been described for measuring the content of thiols in living cells during the cell cycle by flow cytometry, by Poot, et al., Flow Cytometric Analysis of Cell Cycle-Dependent Changes in Cell Thiol Level by Combining a New Laser Dye With Hoechst 33342, CYTOMETRY 12, 184 (1991). Although the two probes described by Poot, et al. may prove useful for this invention, the specific haloalkylated reagents of Poot et al. were not utilized to detect or quantitate the presence or activity of a second enzyme, other than glutathione transferase, in live or fixed cells or to determine the viability of the cell.

Mangel et al. has described a family of fluorogenic protease substrates having amino acids or peptides bound to the amino nitrogens of a rhodamine fluorophore (U.S. Pat. Nos. 4,557,862 (1985) and 4,649,893 (1987)). Upon cleavage of the amino acids by proteases, the rhodamine becomes fluorescent. However, the Mangel et al. compounds do not possess a haloalkyl moiety to aid in retaining the fluorescent product within cells, and typically leak from cells fairly quickly after enzyme cleavage. The Mangel et al. compounds are also generally difficult to load into cells. This is primarily due to the size of the substrates, but can also be due to the presence of highly polar amino acid residues used as blocking groups. Also, the need for the enzyme to cleave two blocking groups from the substrate complicates the kinetics of the enzyme reaction considerably, as cleavage of the second fluorophore-amino acid bond is much slower than cleavage of the first. Finally, the preparation of the Mangel et al. substrates requires two equivalents of the relatively expensive target peptides for each fluorophore so labeled.

The presence of the haloalkyl group is critical for retention of the reporter molecule in cells. In a direct comparison of a reporter molecule and its chloromethyl-substituted analog, it was found that the chloromethyl-substituted reporter was retained in cells for several hours, while the conventional reporter leaked away quickly (Examples 15 and 16). Similarly, the nature of the haloalkyl group itself is critical. While haloalkyl-substituted hydrolase substrates based on coumarin fluorophores have been described by Scheper et al., (U.S. Pat. No. 4,777,269 (1988)), Scheper et al.'s preferred haloalkyl substituent, trifluoromethyl, does not aid in retaining the reporter molecular within cells. A comparison of cellular retention based on haloalkyl group was performed (Example 16), and verified that the chloromethyl-substituted reporter was well-retained in cells, while the methyl- and trifluoromethyl-substituted reporters show very poor retention.

SUMMARY OF THE INVENTION AND DESCRIPTION OF PREFERRED EMBODIMENTS

Figure 1:
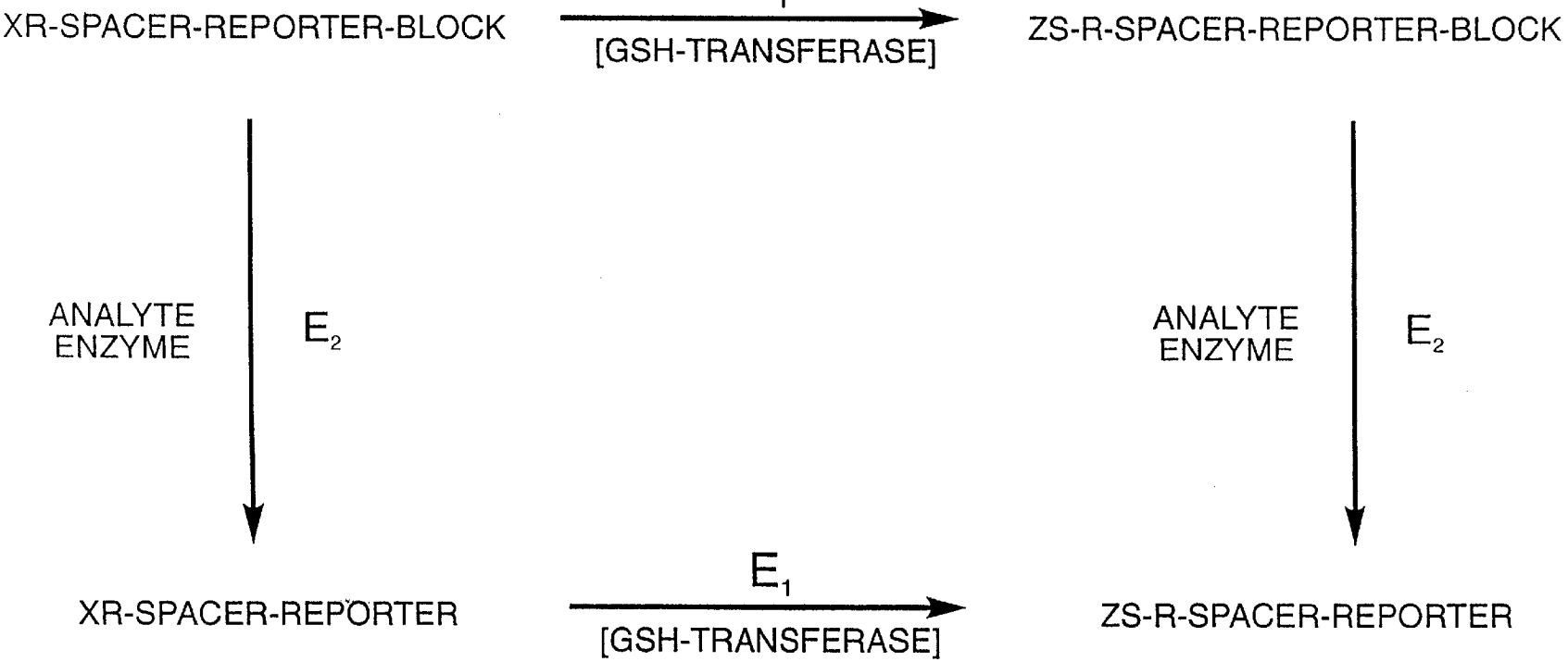
FIG. 1. Diagram of two alternate pathways to formation of a detectable thioether conjugate. $E_1$ is the reaction between the intracellular thiol, which, in the case of glutathione, is catalyzed by glutathione transferase. $E_2$ is the removal of BLOCK resulting from the action of the analyte enzyme.

This invention utilizes novel probes that simultaneously form conjugates with cysteine residues in peptides and act as substrates for an intracellular enzyme whose activity is to be detected. The probes allow the analysis of metabolic activity of living cells under a variety of conditions.

The novel method for analyzing the metabolic activity of cells begins with the preparation of a biocompatible solution containing a substrate. A biocompatible solution is any solution that facilitates the contact between the substrate and the cells being analyzed without destroying the integrity of the cell membrane or the viability of the cell. The biocompatible solution may include buffering agents, a culture medium for the cells, solvents or detergents that, without materially harming the cells, assist in solubilizing the substrate or permeabilizing cell membranes, or combinations thereof. The substrates have the general form:

XR-SPACER-REPORTER-BLOCK

BLOCK is any group that can be removed by specific hydrolytic or oxidative action of the analyte on the bond between BLOCK and REPORTER. The action of the analyte removing BLOCK produces a detectable product with emission or excitation properties different from those of the substrate, i.e. as a result of action by the analyte on the substrate, REPORTER exhibits a detectable change in absorbance or, preferably, fluorescence. Usually action of the analyte removing BLOCK results in a shift in the absorbance of the resultant product to longer wavelengths that are not absorbed or are minimally absorbed before the removal of BLOCK. BLOCK is selected to be removable only by action of a specific analyte, i.e. an enzyme or chemical substance predetermined to be of analytical interest. BLOCK is only removed when the specific analyte is present.

BLOCK is typically a monovalent moiety derived by removal of a hydroxy group from a phosphate, a sulfate, or a biologically compatible salt thereof. Alternatively BLOCK is a monovalent moiety derived by removal of a hydroxy group from a carboxy group of an aliphatic acid (e.g. acetic or octanoic acid), an aromatic acid (e.g. p-guanidinobenzoic acid), an amino acid, a protected amino acid, or a peptide. BLOCK may also be a monovalent moiety derived by removal of a hydroxy group from an alcohol, a mono-, or a polysaccharide (e.g. galactose, glucose, glucuronic acid, cellobiose). Representative hydrolytic enzymes (analytes) and their target groups are given in Table 1. Any of the target groups in Table 1, as well as target groups for other hydrolytic or oxidative enzymes, can be used to derive, by means known in the art, a removable BLOCK to combine with a selected REPORTER molecule.

Although the majority of enzyme substrates that have been described are substrates for hydrolytic enzymes wherein BLOCK is an ester or an amide, fluorogenic substrates for enzymes such as the microsomal dealkylases, including cytochrome P450 that function by an oxidative mechanism are also known. In these cases BLOCK is usually an aliphatic ether. Primary examples include 7-ethoxycoumarin, ethers of resorufin (Nakai, et al., J. BIOL. CHEM. 267, 19503 (1992)) and steroidal ethers U.S. Pat. No. 5,110,725 to Martone et al. (1992)). Because the microsomal dealkylase enzymes typically have low turnover rates in cells, it is difficult to detect the fluorescent product in single cells unless a substrate such as that described in Example 8 is used.

The REPORTER portion of the substrate is a molecule for which the emission or excitation properties change depending on the presence or absence of BLOCK. Preferably, REPORTER is a dye that, except for being bound to BLOCK by a REPORTER-BLOCK bond, is detectable by fluorescence. Commonly REPORTER is a phenol or an aromatic amine and the bond linking REPORTER and BLOCK is an ester of a carboxylic, phosphoric, or sulfuric acid, or a biologically compatible salt thereof, an ether, a thioether, or an amide. Typically the carboxylate ester is an ester of an aliphatic carboxylic acid having 1 to 18 carbon atoms or of an aromatic carboxylic acid having 7 to 24 carbon atoms. The amide bond is commonly formed by the removal of the elements of hydroxy from the carboxylic acid of an amino acid or peptide and a hydrogen atom from an amino moiety on REPORTER. The ether or thioether bond is formed by removal of the elements of hydroxy from an alcohol, preferably a steroidal alcohol having 30 or less carbon atoms, or a lower alcohol having 6 or less carbon atoms, and a hydrogen atom from a phenolic or thiophenolic moiety on REPORTER. Alternatively the ether or thioether bond is formed by removal of hydroxy from a mono- or polysaccharide and a hydrogen atom from a phenolic or thiophenolic moiety on REPORTER.

A biologically compatible salt is not toxic as used, and does not have a substantially deleterious effect on biomolecules. Examples of biologically compatible anionic salts include, among others, chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Examples of biologically compatible cationic salts include, among others, sodium, potassium, ammonium, and alkylammonium. Preferred salts are chloride, iodide, perchlorate, various sulfonates, sodium and potassium.

TABLE 1

REPRESENTATIVE ENZYMES

| E.C. NO. | ENZYME | TARGET GROUP |
|---|---|---|
| 3.2.1.20 | α-Glucosidase | α-D-Glucose |
| 3.2.1.21 | β-Glucosidase | β-D-Glucose |
| 3.2.1.22 | α-Galactosidase | α-D-Galactose |
| 3.2.1.23 | β-Galactosidase | β-D-Galactose |
| 3.2.1.24 | α-Mannosidase | α-D-Mannose |
| 3.2.1.25 | β-Mannosidase | β-D-Mannose |
| 3.2.1.30 | N-Acetyl-β-D-Glucosamidase | β-D-N-Acetyl-Glucosamine |
| 3.2.1.31 | β-Glucuronidase | β-D-Glucoronic Acid |
| 3.2.1.38 | β-D-Fucosidase | β-D-Fucose |
| 3.2.1.51 | α-L-Fucosidase | α-L-Fucose |
| 3.2.1-- | β-L-Furosidase | β-L-Fucose |
| 3.2.1.76 | L-Iduronidase | α-L-Iduronic Acid |
| 3.2.1.4 | Cellulase | β-D-Cellobiose |
| 3.2.1-- | α-Arabinopyranosidase | α-L-Arabinopyranose |
| 3.2.1.37 | β-Xylosidase | β-D-Xylose |
| 3.2.1.18 | α-N-Acetyl-neuraminidase | α-D-N-Acetyl-neuraminic acid (Sialic acid) |
| 3.1.1-- | guanidinobenzoatase | aryl esters of p-guanidinobenzoate |
| 3.1.3.1 | alkaline phosphatase | aryl or alkyl phosphate monoesters |
| 3.1.3.2 | acid phosphatase | aryl or alkyl phosphate monoesters |
| 3.1.6.1 | aryl sulfatase | aryl sulfate monoesters |
| 3.3.3.41 | 4-nitrophenylphosphatase | aryl phosphates |
| 3.4.11.1 | leucine amino peptidase | leucine residues at α-carboxyl |

Many dyes suitable for use in the novel substrates have been described previously. Among the most common are derivatives of coumarin such as 7-hydroxy-4-methylcoumarin (β-methylumbelliferone) or 7-amino-4-methylcoumarin, 2-amino-4-methoxynaphthalene, 1-hydroxypyrene, fluorescein and resorufin. Also suitable for some applications are phenalenones or benzphenalenones U.S. Pat. No. 4,812,409), acridinones (U.S. Pat. No. 4,810,636), anthracenes, rhodamines, rhodols, or various derivatives of α- and β-naphthol. Table 2 describes some representative dyes which can be used to make the subject substrates.

TABLE 2

REPRESENTATIVE REPORTER MOLECULES

| Reporter Molecules | Sample Substrate |
|---|---|
| 6-aminobenzphenalenones | 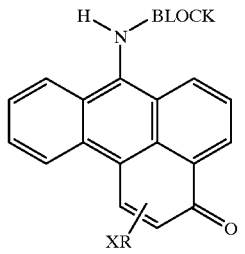 |

TABLE 2-continued
REPRESENTATIVE REPORTER MOLECULES
| Reporter Molecules | Sample Substrate |
|---|---|
| 7-aminocoumarin | 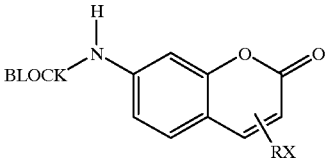 |
| 6-aminophenalenone | 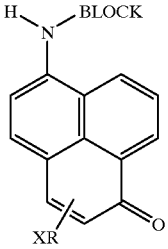 |
| anthracene | 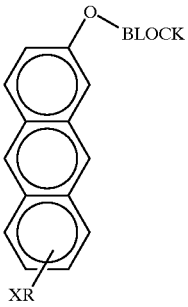 |
| fluorescein | 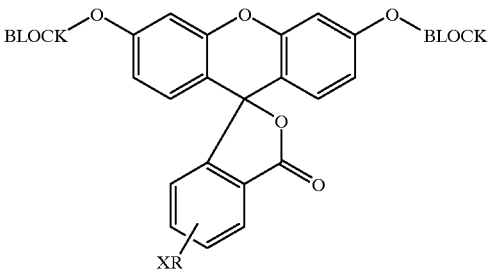 |
| 6-hydroxybenzphenalenones | 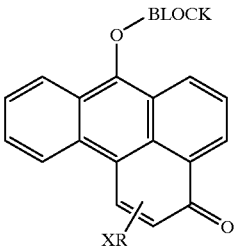 |
| 7-hydroxycoumarin | 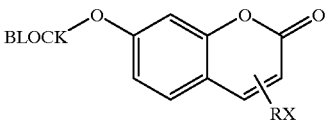 |

TABLE 2-continued
REPRESENTATIVE REPORTER MOLECULES
| Reporter Molecules | Sample Substrate |
|---|---|
| 6-hydroxyphenalenone | 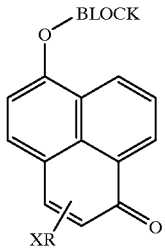 |
| 4-methoxy-2-naphthyl amine | 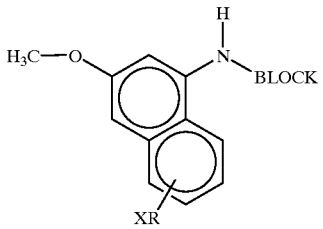 |
| resorufin | 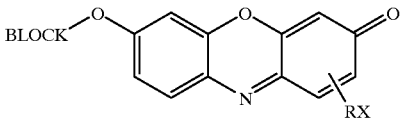 |
| rhodamine, type I | 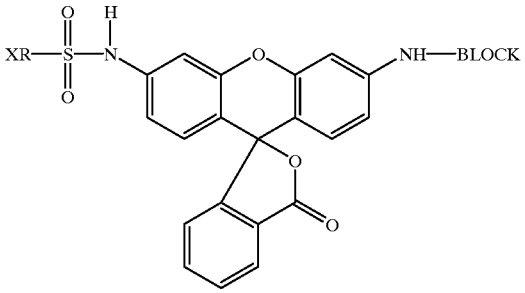 |
| rhodamine, type II | 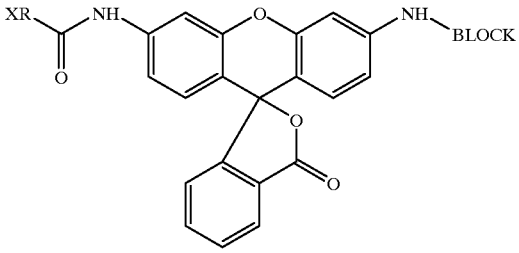 |
| rhodamine, type III | 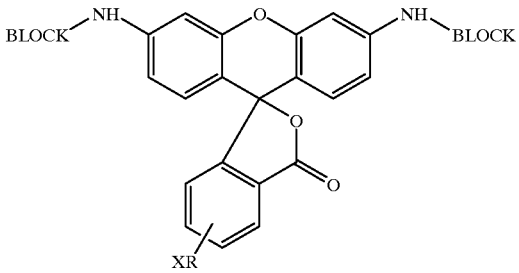 |

TABLE 2-continued

REPRESENTATIVE REPORTER MOLECULES

| Reporter Molecules | Sample Substrate |
|---|---|
| rhodol, type I | 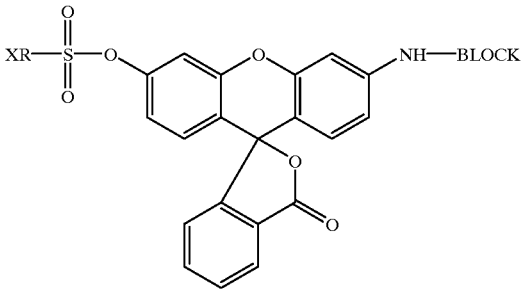 |
| rhodol, type II | 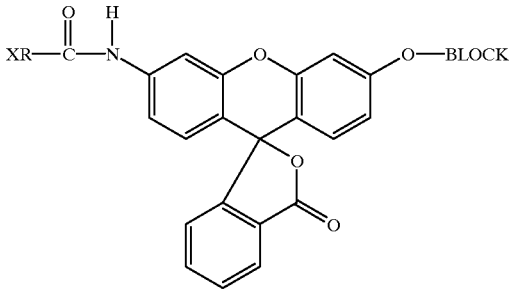 |
| rhodol, type III | 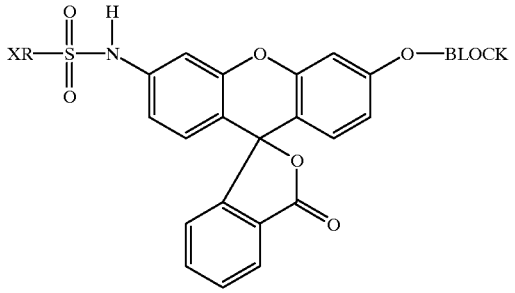 |
| acridinone | 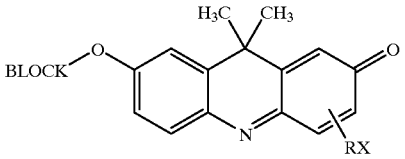 |

A third component of the subject substrate is a haloalkyl moiety XR-, where X is a halogen and R is an alkyl linkage having 1–4 carbon atoms. Preferably the halogen is Cl or Br, and R is methylene; more preferably XR- is $ClCH_2$—. It is recognized that many substituents such as haloaryl, epoxides, sulfonate esters and similar functional groups that contain a group that is readily replaced in a reaction with thiols such as glutathione, that may or may not be catalyzed by glutathione transferase, are equivalent to XR- for some applications.

Typically XR- is attached to the aromatic system of the REPORTER moiety directly. In these embodiments of the invention, SPACER is preferably a single covalent bond. In another embodiment of the invention, the reactive sites XR- and BLOCK are separated from each other in their attachment to REPORTER. To provide this separation XR- is attached to REPORTER by a SPACER moiety, to yield a compound of the formula XR-SPACER-REPORTER-BLOCK. In this embodiment, XR- is typically attached to REPORTER via conjugation to a heteroatom present on REPORTER, such as a fluorescein oxygen or rhodamine nitrogen, and SPACER is a covalent linkage having 0–8 carbon atoms and 1–4 heteroatoms, where the heteroatoms are O, N or S in any combination. Preferably, SPACER is carbonyl (—(C═O)—), sulfonyl (—$SO_2$—), benzoyl (—$C_6H_4$—(C═O)—), where the carbonyl is attached to the phenyl ring at the ortho, metal, or para position with respect to XR-, or benzenesulfonyl (—$C_6H_5$—$SO_2$—), where the sulfonyl is attached to the phenyl ring at the ortho, meta, or para position with respect to XR-.

Where REPORTER is a rhodol fluorophore, BLOCK is optionally a mono- or polysaccharide, phosphate, sulfate, ester or ether attached to the rhodol oxygen, or an amino acid or peptide attached to the rhodol nitrogen, and XR-SPACER is optionally attached to the remaining nitrogen or oxygen, respectively (as illustrated above; rhodols type I, II and III). Where REPORTER is a rhodamine fluorophore, both BLOCK and XR-SPACER are optionally attached to rhodamine nitrogens (as illustrated above: rhodamines type I and II). Where REPORTER is either a rhodol or rhodamine fluorophore, XR- is optionally attached directly to the aromatic ring at the 5- or 6-position of the fluorophore, and the fluorophore is further substituted by two BLOCK groups (as illustrated above; rhodamine type III).

Rhodamine-based substrates having only a single amino acid or peptide are smaller or less polar than bis-substituted rhodamines, and can subsequently enter cells with greater facility. Additionally, the removal of only a single BLOCK results in a fluorescent product, simplifying the kinetics of enzyme activity. Finally, less of the typically expensive amino acid BLOCK is used per fluorophore.

Rhodol-based substrates having an XR-SPACER on either the terminal O or N atom and an enzyme-removable BLOCK on the remaining terminal O or N are also smaller and less polar than substrates based on fluorescein or rhodamine 110. Furthermore, only a single enzymatic reaction is required to generate a fluorescent product from the substrates.

Once inside the cell, the haloalkyl moiety (XR-) will covalently react with an intracellular thiol (Z-S-H) to form a thioether conjugate (Z-S-R). The term intracellular thiol includes glutathione and other polar or higher molecular weight thiols present in cells such as cysteine and cysteine-containing peptides and proteins. Reaction of the subject substrates with thiols other than gluthione appears to be more common with the more reactive alkylating groups (XR) such as bromomethyl and iodomethyl. Where the thiol is glutathione, formation of the thioether conjugate is likely to be catalyzed by the enzyme glutathione transferase, but glutathione transferase is not essential for utilization of these substrates, provided that the uncatalyzed reaction with intracellular thiols is sufficiently rapid to yield retention of at least some of the fluorescent product inside cells. However, a reaction of the chloroalkylated substrates with glutathione that is catalyzed by glutathione transferase is preferred since nonspecific reaction of protein thiols with alkylating agents is more likely to result in cytotoxicity.

After a biocompatible solution of substrate has been prepared, the substrate in solution is placed in contact with the cells being analyzed. The cells being analyzed may be from any plant or animal origin that is suspected of containing the analyte, including single cell organisms such as bacteria and yeast. The cells may be present in an intact organism or in a medium that has been separated from the organism, such as biological fluids or cultures of essentially pure cell lines. The analyte may have been introduced into the cell by processes of genetic engineering familiar to one skilled in the art. The analyte, if present, may be localized in one or more intracellular areas or organelles, which may include the inner membrane of the cell, the cytosol, microsomes, mitochondria, liposomes, or the nucleus.

The substrate is brought into contact with the analyte enzyme under conditions where the substrate can readily enter intracellular areas which may contain the analyte of interest. The substrate enters intracellular areas by any technique that is suitable for transporting the substrate into the intracellular areas with minimal disruption of the viability of the cell and integrity of cell membranes. Examples of suitable processes include passive diffusion through the membrane; action of chemical agents such as detergents, enzymes or adenosine triphosphate; receptor- or transport protein-mediated uptake; pore-forming proteins; microinjection; electroporation; hypoosmotic shock (Example 12); or minimal physical disruption such as scrape loading or bombardment with solid particles coated with or in the presence of the substrate. Depending on the technique used to introduce the substrate into the cells and the REPORTER portion of the substrate, it may take a few seconds to several hours for enough substrate to enter the cells to give a detectable result.

After the substrate enters the cell, sufficient time is allowed for the specific action of the analyte to remove BLOCK, and for the haloalkyl XR to react with a thiol. The formation of the detectable conjugate REPORTER-SPACER-R-S-Z can occur by either of two routes (FIG. 1). In Route 1 a probe whose detectable optical property is blocked, reacts with an intracellular thiol to form a blocked intermediate that is not yet detectable, at least at the optimal wavelength for detection. If the analyte is present and active, BLOCK is removed by action of the analyte. This action results in formation of the detectable reporter molecule which, because of its conjugation to the thiol and resultant charge, is well retained intracellularly. In Route 2 action of the analyte removes BLOCK from the substrate first, resulting in formation of a detectable haloalkylated reporter molecule. In a subsequent step, the detectable molecule is conjugated to an intracellular thiol resulting in formation of the identical reporter molecule conjugate as formed in Route 1. Conjugation of the haloalkyl moiety to glutathione or low molecular weight peptide converts the REPORTER molecule into a small peptide, REPORTER-SPACER-R-S-Z, that has the charge and approximate permeability properties of an amino acid, while having the detectability of the REPORTER molecule. Since amino acids and most peptides are generally not freely permeant to intact cell membranes, it is important for retention of the reaction product that this conjugation occurs intracellularly.

In most cases, the intracellularly thiol is glutathione, and the conjugation is catalyzed by the enzyme glutathione transferase. Example 14 presents evidence that the metabolic products are substrates for glutathione transferase and presents methods for determined the activity of glutathione transferase in vitro. The relative importance of the two routes to the same product depends on the concentrations and activities of the enzymes and substrates, the access of the substrates to the enzymes, the concentration of intracellular thiols, particularly glutathione, the reactivity of the haloalkyl moiety, and other factors. Significantly, in both cases formation of the detectable reporter molecule occurs only following action of the analyte. Thus, even though conjugation of the substrate to an intracellular thiol improves retention of BLOCK-REPORTER in the cell, it does not result in formation of a detectable reporter molecule unless the enzyme needed to remove the BLOCK is present and active. When the analyte is present, the fluorescent product is typically visible within a few minutes. Optimal accumulation of the thioether conjugate may be obtained within 15 minutes to 1 hour, however detectability remains for hours to days.

Once sufficient time for the unblocking and conjugation has elapsed, the cells are prepared for measuring fluorescence or absorbance. The preparation required will depend on the method to be used to make such measurements. The preparation typically involves the transfer of cells from the biocompatible solution containing the substrate to a fresh biocompatible solution without substrate, usually a standard culture medium, and washing the cells to remove extracellular products. Then the cells may be placed in or on the appropriate container for making the measurements, such as cuvettes, culture dishes, slides, etc. Unlike the use of most fluorescent substrates, the method using the subject substrates may also include fixing the cells using an aldehyde fixative. Where the REPORTER-thiol adduct possesses an aliphatic amine group, as in the case of a glutathione adduct, this group makes the detectable adduct capable of fixation by common aldehyde fixatives such as formaldehyde and glutaraldehyde without complete dispersion of the fluorescence (Example 11). Thus it is possible to determine the presence of the analyte in cells after a variable or fixed period following the killing and fixation of the cells. This reduces the hazard of working with pathogenic cells. This property is also useful for detecting the effect of cytotoxic agents or conditions.

The final step of the subject method for analyzing the metabolic activity of cells in making qualitative or quantitative measurements of absorbance or fluorescence of REPORTER. The REPORTER is typically present as part of the thioether conjugate retained inside the cell. REPORTER may be blocked or unblocked, depending on whether the analyte was present in the cells. The measurements can be made by observation of the absorbance or fluorescence through visual inspection or by using a suitable instrument such as an absorption spectrometer, fluorometer, flow cytometer or microscope. Analysis may be of the whole organism, a tissue, a cell suspension, adherent cells or single cells. Analysis can be of the REPORTER conjugate located in intact living cells (Examples 11–13), in cells that have been fixed with an aldehyde fixative in a manner so as to retain the REPORTER in the fixed cell (Example 11) or can be of the supernate that results from lysis of the cell by a lysing agent. In the latter case, detection in the supernate may be correlated with both metabolism of the BLOCK-REPORTER and the activity of the lysing agent (Example 15). In the case of single cells, whether live or fixed, the analysis may be by imaging or flow cytometry, where the fluorescene of REPORTER in the cell may be used to discriminate or isolate the cell based on the presence or level of activity of an analyte, using techniques well known in the art, as described by Melamed, et al., FLOW CYTOMETRY AND SORTING (2nd ed. 1990); Shapiro, PRACTICAL FLOW CYTOMETRY (1985).

The fluorescent thioether conjugate formed by metabolic removal of BLOCK and conjugation of REPORTER to glutathione is retained inside living cells for sufficiently long to quantitatively or qualitatively measure the fluorescence or absorbance of the attached REPORTER. When the integrity of the membranes is disrupted, however, the reaction products may easily leak from the cell unless a fixing agent is present (Example 11). The change in fluorescence intensity that results from loss of the detectable product in therefore a useful means of detecting cell death, especially when caused by cytotoxic agents. Metabolism of the substrate to a polar tracer by cells that are positive for the enzymes that remove BLOCK is the basis of a test for cytotoxicity of extrinsic reagents (Example 15) or extrinsic conditions such as heat. For instance, glucosidase is an enzyme that is commonly found in many cells, making the subject glucosidase substrates also useful for this application. In other cases it may be preferred to label cells that have an enzymatic activity that is not present in all cells so that selective determination of cytotoxicity in a mixed cell population can be detected. In this case substrates such as the galactosides, glucuronides and phosphates are preferred since these enzymes are not as widely distributed, particularly in mammalian cells.

EXAMPLES

The examples illustrate that the subject substrates XR-SPACER-REPORTER-BLOCK may be derived from a variety of fluorophores (Examples 1–10) with a range of spectral properties from the near ultraviolet to about 650 nm and that the BLOCK group may be any of several groups that can be removed by action of a specific analyte (Examples 1–10). Methods for synthesis of the REPORTER-BLOCK conjugates are similar or identical to those of the structurally similar molecules that do not contain the chloroalkyl groups. For instance 7-hydroxy-4-chloromethylcoumarin (Example 2) and 7-hydroxy-4-methylcoumarin (β-methylumbelliferone) have similar structures and reactivity and numerous glycosidase phosphatase, sulfatase, ether, ester, guanidinobenzoatase have been derived from the latter compound. Fluorescein and 5-chloromethylfluorescein (Example 1) have similar reactivity, so that synthetic methods for one REPORTER molecule and its chloroalkylated derivative proceed similarly. The examples illustrate materials that can be used to perform the process that is the subject of the invention and not to limit or exclude reagents that can be prepared by one reasonably skilled in the art that are essentially equivalent. Furthermore, haloalkylated REPORTERS are typically synthesized using the same or similar chemistry as is used to prepare non-haloalkylated REPORTERS by the substitution of a haloalkyl moiety on one of the reactants (Examples 2 and 6). Alternatively, haloalkylated REPORTERS can be prepared by the conversion of other residues present on REPORTER, such as carboxylic acids, to haloalkyl by methods well known in the art (Example 1).

The examples also indicate that the subject substrates are advantageous for measurement of the enzymatic activity in single cells in that they are permeable to the intracellular organelle containing the enzyme (Examples 11–13 and 15), they are converted to a detectable reporter molecule by specific action of the enzyme (Examples 11–13 and 15), the reporter molecule is retained under physiological conditions for the period required for its detection (Example 11–13 and 15), a direct relationship between the enzymatic activity and the amount of dye retained in the cell can be established (Example 13), and the reporter molecule and the substrate are substantially non-toxic to the cells (Example 11–13). In addition, while not essential for utility, the reporter molecule is still detectable flowing fixation of the cell (Example 11).

Example 1

PREPARATION OF A β-GALACTOSIDASE SUBSTRATE HAVING A CHLOROMETHYL GROUP AT THE 5-POSITION AND GALACTOSIDES ON THE 3'- AND 6'-HYDROXYL POSITIONS OF FLUORESCEIN

The following compound is prepared:

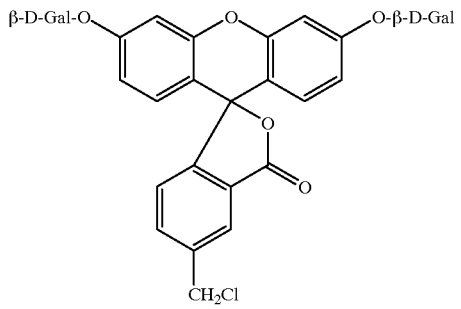

Preparation of 5-acetoxymethylfluorescein diacetate:

A solution of 5-carboxyfluorescein diacetate (Molecular Probes, Eugene Oregon) (18.4 g, 40 mmoles) and triethylamine (5.7 g, 56 mmoles) in tetrahydrofuran (400 mL) is cooled to −5° C. A solution of ethyl chloroformate (4.3 g, 40 mmoles) in tetrahydrofuran (50 mL) is added dropwise to the stirred mixture was 30 minutes. This reaction mixture is stirred for another 30 minutes at −5° C., allowed to reach +5° C., and sodium borohydride (5.8 g, 150 mmoles) is added portionwise, followed by dropwise addition of methanol (25 mL) to the stirred mixture at 5° C. over 30 minutes. The reaction mixture is allowed to come to room temperature and acidified to pH 2 by dropwise addition of 6M aqueous HCl. The precipitated salts are filtered and rinsed with tetrahydrofuran (2×50 mL). The filtrate is evaporated to yield an orange solid, which is added to a solution of acetic anhydride (100 mL) containing pyridine (50 mL). This mixture is heated to reflux until the orange color disappears. Solvents are evaporated and the residue is dissolved in 200 mL of ethyl acetate. The solution is extracted 3 times with cold 5% HCl, then three times with cold water, and then is dried over anhydrous sodium sulfate. The drying agent is removed by filtration and the filtrate is evaporated to yield the crude product as a colorless solid (90%), which can be purified by column chromatography on silica gel by gradient elution using 30–50% acetone in hexanes. TLC (1:1 ethyl acetate:hexanes) $R_f$=0.5.

Preparation of 5-chloromethylfluorescein (CMF):

5-Acetoxymethylfluorescein (4.9 g, 10 mmoles) is dissolved with heating and stirring in acetic acid (200 mL). Concentrated hydrochloric acid (200 mL) is added gradually. The mixture is heated to reflux for 15 hours and the solvents are evaporated. Concentrated hydrochloric acid (400 mL) is again added to the residue and heating to reflux with stirring is continued for another 15 hours. The reaction mixture is cooled to room temperature, crushed ice is added (500 mL) and the pH is increased to about 2–3 by gradual addition of aqueous 1M sodium hydroxide solution. The resulting orange solid is filtered and washed with water. The product is chromatographed on a column of silica gel G using solution of 5% methanol in chloroform for flash elution. Fractions containing the product are combined to give an orange-yellow solid (3 g, 80%). TLC on silica gel (1:15:84 acetic acid:methanol:chloroform) $R_f$=0.6.

Preparation of 5-chloromethylfluorescein di-β-D-galactopyranoside, octaacetate:

A mixture of 5-chloromethylfluorescein (150 mg, 0.394 mmole), powdered 4 Å molecular sieve (0.5 g), sym-collidine (130 μL, 0.98 mmole), and dry silver carbonate (135 mg, 0.49 mmole) in anhydrous acetonitrile (10 mL) is allowed to stir in the dark for 1 hour at room temperature under an atmosphere of dry nitrogen gas. 1-Bromo-2,3,4,6-tetra-O-acetyl α-D-galactopyranoside (405 mg, 0.98 mmole) is added slowly with stirring. The mixture is allowed to stir as described above for 96 hours, after which it is filtered through a pad of diatomaceous earth. The precipitate is washed with chloroform (5×15 mL). The combined filtrates are extracted sequentially with 1M aqueous hydrochloric acid solution (1×75 mL), saturated aqueous sodium bicarbonate solution (1×75 mL), 0.1M aqueous sodium thiosulfate solution (1×75 mL) then water (1×75 mL). The combined organic layers are dried over anhydrous sodium sulfate, filtered, evaporated and dried in vacuo to a bright yellow foam (620 mg). This crude intermediate is applied to a column of silica gel G (44×440 mm) and eluted by gradient elution using 5% to 20% acetonitrile in chloroform as eluent. Fractions containing the first UV absorbing component to elute from the column are combined and evaporated to a colorless powder (60 mg, 15%). TLC (19:1 chloroform:methanol) $R_f$=0.78. $^1$H-n.m.r.($CDCl_3$) δ: 8.04(s, 1H); 7.71 (dd, 1H); 7.14 (d, 1H); 6.89 (dd,2H), 6.73–6.70 (m,4H); 5.50–5.46 (m,4H); 5.14–5.07 (m,4H); 4.72 (s,2H, —$CH_2$Cl); 4.25–4.08 (m,6H); 2.19,2.12,2.06,2.02 (4×s,3H each).

Preparation of 5-chloromethylfluorescein di-β-D-galactopyranoside (CMFDG):

A suspension of 5-chloromethylfluorescein di-β-D-galactopyranoside, octaacetate (60 mg, 58 μmoles) in anhydrous methanol (15 mL) is cooled to 0° C. in an ice bath while under an atmosphere of dry nitrogen gas. A solution of freshly prepared sodium methoxide in methanol (20 μL, 0.75M solution) is added, and this mixture is allowed to stir at 0° C. for 2.15 hours. The reaction is neutralized with washed, dry Amberlite IRC50 ($H^+$) resin (pH 4), filtered and evaporated to approximately 25 mL total volume. The product is crystallized by addition of anhydrous diethyl ether (150 mL) and stored at −12° C. The colorless crystalline product is isolated by filtration through a Nylon 66 membrane filter (0.45 pore size), washed with fresh diethyl ether and dried in vacuo to an off-white powder (1st crop, 15 mg, 37% ). Thin layer chromatography (TLC) (7:1:1:1 ethyl acetate:methanol:water:acetic acid) $R_f$=0.31; (3:1:1 n-butanol:methanol:water) $R_f$=0.56. $^1$H NMR spectroscopy ($d_6$-DMSO) δ: 8.10(s, 1H); 7.86(d, 1H); 7.35(d, 1H); 7.00(d, 2H); 6.80–6.68(m,4H); 5.47(dd,2H,2×H); 5.20(m,2H,2×—OH); 4.98(s,2H,—$CH_2$Cl); 4.97(m,2H); 4.88(m,2H); 4.70 (m,2H); 4.51(d,2H); 3.73–3.20(m,10H).

Example 2

PREPARATION OF A SUBSTRATE HAVING A PHOSPHATE BLOCKING GROUP AT THE 7-POSITION AND A CHLOROMETHYL GROUP AT THE 4-POSITION OF COUMARIN

The following compound is prepared:

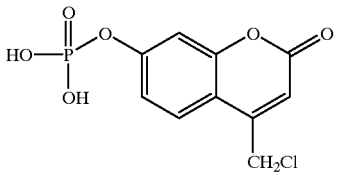

Preparation of 4-chloromethyl-7-hydroxycoumarin:

Ethyl 4-chloroacetoacetate (9.38 g, 56.99 mmoles) containing resorcinol (6.27 g, 56.99 mmoles), is slowly added to 4.99 mL (59.88 mmoles) concentrated sulfuric acid. The resulting solution is stirred for 20 min. after which time the starting materials have been consumed (silica gel thin layer chromatography (TLC) (1521 chloroform:methanol). The reaction mixture is poured into 50 mL crushed ice, and the resulting precipitate is triturated five times with 50 mL 0° C. ice-$H_2O$ to yield a semicrystalline solid which is dried in vacuo (8.66 g, 72% yield). Silica gel TLC analysis of this material shows one major product with an $R_f$ of 0.48 (15:1 chloroform:methanol). In addition, 2.0 g of this material is purified on a 4 cm×15 cm column of 35–70 $\mu$m silica gel. Elution is carded out by a stepwise gradient starting with chloroform (500 mL) and finished with 9:1 chloroform-:methanol (500 mL). Ten 100 mL fractions are collected and monitored by silica gel TLC (15:10 chloroform:methanol). Fractions containing the pure product are combined, evaporated and dried (1.1 g, 55% recovery, 40% yield). $^1$H NMR spectroscopy (DMSO-$d_6$) δ4.95 (s, 2H); 6.42 (s, 1H); 6.75 (s, 1H); 6.85 (d, 1H); 7.67 (d, 1H). Melting point=143° C.

Preparation of 4-chloromethyl-7-coumarinylphosphate:

To a solution of 4-chloromethyl-7-hydroxycoumarin (211 mg, 1.0 mmole) in dry pyridine (5 mL) at 0° C. under dry $N_2$ (g), is added a solution of phosphorus oxychloride (0.105 g, 1.0 mmole) in pyridine (1.0 mL) at 0° C. The reaction is rapid; by silica gel TLC (15:1 chloroform:methanol and 7:1:1:1 ethyl acetate:methanol:$H_2O$:acetic acid) it is determined that the starting materials have been consumed. The reaction mixture is then poured into 15 mL crushed ice, extracted with 5×50 mL ether, and lyophilized from $H_2O$. This material is then purified by chromatographic separation on a column of lipophilic SEPHADEX LH 20 (3×45 cm). Elution is carried out with $H_2O$. The product containing fractions are lyophilized. $^1$H NMR spectroscopy (DMSO-$d_6$) δ5.0 (s, 2H); 6.60 (s, 1H); 7.20–7.30 (s, 1H); 7.40–7.50 (d, 1H); 7.80–7.90 (d, 1H).

Example 3

PREPARATION OF A SUBSTRATE HAVING A GALACTOPYRANOSIDE BLOCKING GROUP AT THE 7-POSITION AND A CHLOROMETHYL GROUP AT THE 4-POSITION OF COUMARIN

The following compound is prepared:

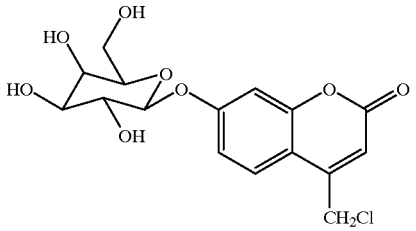

Preparation of 7-(2,3,4,6-tetra-O-acetyl β-D-galactopyranosyloxy)-4-chloromethylcoumarin:

A mixture of 7-hydroxy-4-chloromethylcoumarin (107 mg, 0.51 mmole), activated 3 Å molecular sieves (0.5 g), sym-collidine (100 $\mu$L, 0.76 mmole) and silver carbonate (208 mg, 0.75 mmole) in anhydrous dichloromethane (4 mL) is allowed to stir in the dark at room temperature for 1 hour. 1-Bromo-2,3,4,6-tetra-O-acetyl α-D-galactopyranoside (316 mg, 0.77 mmole) is added slowly over a period of 20 minutes, and the mixture is allowed to stir as described above for 18 hours. The reaction mixture is filtered through a pad of diatomaceous earth. The precipitate is washed with chloroform (5×10 mL), and the combined organic filtrates are extracted with 1M aqueous HCl (1×75 mL), saturated aqueous sodium carbonate solution (1×75 mL), 1M sodium thiosulfate (1×75 mL), and water (1×75 mL). The organic layer is dried over anhydrous sodium sulfate, filtered, and evaporated under reduced pressure to a pale yellow oil (400 mg). The oil is applied to a column of silica gel G (100 g) and eluted by gradient elution using 0–10% ethyl acetate in chloroform. Fractions containing the first UV absorbing component to elute from the column are combined and evaporated to a colorless foam (256 mg, 93%). T.l.c. ($SiO_2$) (8:2 chloroform:ethyl acetate) $R_f$=0.37. $^1$H-n.m.r. ($CDCl_3$) δ: 7.6(d, 1H); 7.3(s, 1H); 7.0(dd, 1H); 6.5(s, 1H); 5.55(d, 1H,H-1); 5.5(d, 1H); 5.2(m,2H); 4.6(s, 2H,—$CH_2Cl$); 4.3–4.0(m,3H); 2.28(s,3H); 2.20(s,3H); 2.15 (s,3H); 2.08 (s,3H).

Preparation of 7-(β-D-galactopyranosyloxy)-4-chloromethylcoumarin (Cl-MUG):

A suspension of dry 7-(2,3,4,6-tetra-O-acetyl-β-D-galactopyranosyloxy)-4-chloromethylcoumarin (250 mg, 0.46 mole) in anhydrous methanol (40 mL) is cooled to 0° C. in an ice-bath while under an atmosphere of dry nitrogen gas. A solution of freshly prepared sodium methoxide in methanol is added (1.0 mL, 0.77M solution) and this mixture is allowed to stir at 0° C. for 1 hour then at ambient temperature for 1.5 hours. The reaction is neutralized to pH 4 with AMBERLITE IRC 50 (H+) resin then filtered, with the resin being washed with methanol 5×10 mL). The combined filtrates are evaporated to dryness and dried in vacuo to a white foam (200 mg), which is recrystallized from methanol:diethyl ether (1:10, 250 mL) to yield a colorless powder (166 mg, 96%) T.l.c. ($SiO_2$) (6:4 ethyl acetate:methanol) $R_f$=0.53. $^1$H NMR spectroscopy ($D_2O$+10% $d_6$-DMSO) δ: 7.9(d, 1H); 7.2(m,2H), 6.6(s, 1H), 5.2(d, 1H,H-1); 4.9(s,2H,—$CH_2Cl$); 4.6(d, 1H,H-4), 4.0–3.4(m, 5H).

Example 4

PREPARATION OF A SUBSTRATE HAVING A GLUCURONIC ACID BLOCKING GROUP AT THE 7-POSITION AND A CHLOROMETHYL GROUP AT THE 4-POSITION OF COUMARIN

The following compound is prepared:

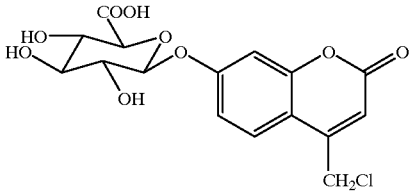

Preparation of 4-chloromethyl-7-coumarinyl-(2,3,4-tri-O-acetyl β-D-glucopyranosiduronide, methyl ester):

A mixture of 7-hydroxy-4-chloromethylcoumarin (520 mg, 2.47 mmole) and powdered 4 Å molecular sieves (0.5 g) are suspended in anhydrous dichloromethane (25 mL), and allowed to stir under dry nitrogen gas for 0.25 hours. Sequentially, anhydrous sym-collidine (489 μL, 3.7 mmole), dry silver carbonate (1.02 g, 3.7 mmole) and 1-bromo-2,3,4-tri-O-acetyl-α-D-glucopyranosiduronic acid, methyl ester (1.47 g, 3.7 mmole) are each added slowly with stirring to the above mixture. This mixture is allowed to stir protected from light at room temperature under an atmosphere of dry nitrogen for 96 hours. The reaction mixture is filtered through a pad of diatomaceous earth. The precipitate is washed with chloroform (5×15 mL) and the combined filtrates sequentially are extracted with 1M aqueous HCl (1×100 mL), saturated aqueous sodium bicarbonate solution (1×100 mL), saturated sodium carbonate solution (1×100 mL), 0.1M sodium thiosulfate solution (1×100 mL) and water (1×100 mL). The combined organic layers are dried over anhydrous sodium sulfate, filtered, evaporated, and dried in vacuo to a tan foam. This is applied to a column of silica gel G (100 g) and eluted by gradient elution using 0–5% ethyl acetate in chloroform as eluent. Fractions containing the first UV absorbing product to elute from the column are combined and evaporated to a colorless foam (560 mg, 43%). T.l.c. (19:1 chloroform:ethyl acetate) $R_f$=0.81; (8:2 chloroform:ethyl acetate) $R_f$=0.39.

Preparation of 4-chloromethyl-7-coumarinyl β-D-glucopyranosiduronide, methyl ester:

A suspension of 4-chloromethylcoumarin 7-(2,3,4-tri-O-acetyl β-D-glucopyranosiduronate, methyl ester (560 mg, 1.06 mmole) in anhydrous methanol (50 mL) is cooled to 0° C. in an ice-bath under an atmosphere of dry nitrogen gas. A solution of freshly prepared sodium methoxide is added in two portions (2×500 μL, 1.37M solution) over a period of one hour. This mixture is allowed to stir as above for 2 hours. The reaction is neutralized with washed, dry AMBERLITE IRC 50 ($H^+$) resin (pH 4), filtered, and evaporated to a clear light yellow glass which is dried in vacuo overnight (410 mg, 99%). $SiO_2$ TLC (8:2 ethyl acetate:methanol) $R_f$=0.75.

Preparation of 4-chloromethyl-7-coumarinyl β-D-glucopyranosiduronic acid (Cl-MUGluC):

A solution of 4-chloromethylcoumarin 7-β-D-glucopyranosiduronide, methyl ester (205 mg, 0.53 mmole) in methanol (4 mL) is added to an ice-cold solution of 0.04M LiOH (14.5 mL, 0.58 mmole) and allowed to stir at 0° C. for 9 hours. After neutralization with AMBERLITE IRC 50 ($H^+$) resin, the mixture is filtered. The methanol is evaporated under reduced pressure, and the aqueous solution is lyophilized to a tan powder (300 mg, 78%). An analytical sample is purified by SEPHADEX LH 20 column chromatography (28×250 mm) with elution by water. Fractions containing the second major component to elute from the column are lyophilized to a colorless foam (62 mg from 125 mg applied to the column). TLC ($SiO_2$)(7:1:1:1 ethyl acetate:methanol:water:acetic acid) $R_f$=0.47. $^1H$ NMR spectroscopy ($d_6$-DMSO) is consistent with the proposed structure.

Example 5

PREPARATION OF A SUBSTRATE HAVING TWO GUANIDINOBENZOATE BLOCKING GROUPS AND A CHLOROMETHYL GROUP AT THE 5-POSITION OF FLUORESCEIN

The following compound is prepared:

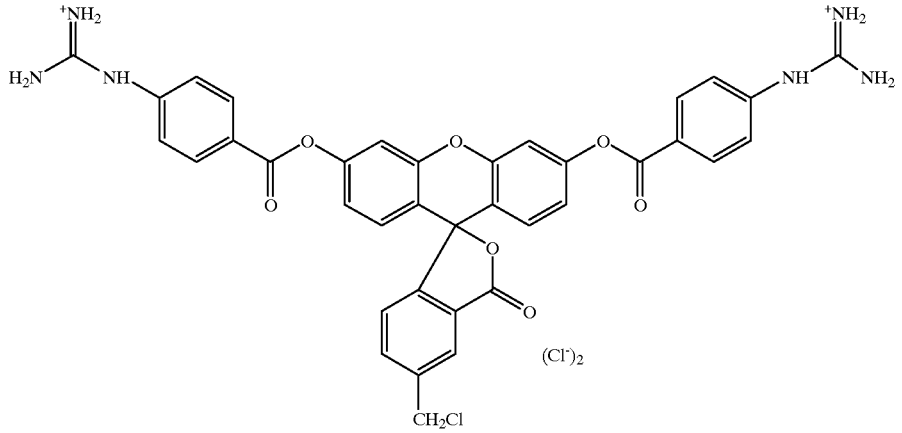

Preparation of 5-chloromethylfluorescein di-guanidinobenzoate:

To a solution of 5-chloromethylfluorescein (30 mg, 79 μmoles) in anhydrous dimethylformamide (5 mL) containing dry sym-collidine (5 mL) is added dicyclohexylcarbodiimide (37 mg, 179 μmoles) and p-guanidinobenzoic acid (43 mg, 199 μmoles). This mixture is allowed to stir at room temperature under an atmosphere of dry nitrogen for 72 hours. The reaction mixture is filtered through a pad of diatomaceous earth. The precipitate is washed with methanol, and the filtrate is evaporated to an oil, which is crystallized by addition of diethyl ether (100 mL). The product is recrystallized from a mixture of chloroform and methanol.

Example 6

PREPARATION OF AMINOCOUMARIN WITH A CHLOROMETHYL GROUP AT THE 4 POSITION

The following compound is prepared:

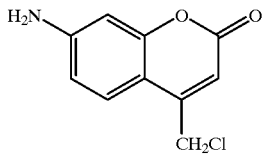

Preparation of 3-hydroxyphenylurethane:

A mixture of m-aminophenol (10 g, 92 mmoles) dry pyridine (10 mL) and dry tetrahydrofuran (THF) (10 mL) is cooled to 0° C. in an ice-bath. Ethyl chloroformate (10 g, 92 mmoles) is added dropwise over 2 hours so that the temperature does not exceed 5° C. After the addition is complete, the ice bath is removed and the reaction mixture is allowed to stir overnight at room temperature. The THF and pyridine are removed under reduced pressure to give a yellow oil, which is dissolved in chloroform (50 mL). The resulting solution is washed with water (200 mL) and followed by saturated NaCl solution and dried over anhydrous sodium sulfate. The chloroform is removed under reduced pressure to yield yellow oil which is triturated with toluene (5 mL), and cooled overnight at 4° C. The shiny, colorless crystals are filtered, washed with cold toluene and dried. Yield: 84%.

Preparation of 7-carbethoxyamino-4-chloromethylcoumarin:

A suspension of ethyl 3-hydroxyphenylurethane (1.81 g, 0.01 mmole), ethyl 4-chloroacetoacetate (1.81 mL, 0.011 mole) and 70% $H_2SO_4$ (50 mL) is stirred for 4 hours at room temperature. The clear solution is poured into 400 mL of ice-water, with constant stirring, to yield a yellowish precipitate. The solid is filtered, washed with water and dried. The product is recrystallized from methanol to give colorless needles (86%).

Preparation of 7-amino-4-chloromethylcoumarin:

A mixture of 7-carbethoxyamino-4-chloromethylcoumarin (2.81 g, 0.01 mole), concentrated sulfuric acid (10 mL) and glacial acetic acid (10 mL) is heated at 130° C. in an oil bath for 1 hour. On cooling, a yellow precipitate is deposited. The mixture is poured into 200 mL of ice-water and left overnight. The resulting solution is made slightly basic (pH 8) with dilute NaOH solution and is then cooled by the addition of ice chips. The yellow precipitate is filtered, washed with water and dried. The product is recrystallized from chloroform to give yellow needles. Yield: 79%.

Several papers have been published on synthesis of the amino acid and peptide amides of 7-amino-4-methylcoumarin that can be used to prepare peptides from 7-amino-4-chloromethylcoumarin, for instance the leucine amide synthesized by Kanaoka, et al, A New Fluorogenic Substrate for Aminopeptidase, CHEM PHARM BULL 25, 603 (1977); the proline amide by Yoshimoto, et al, Post Proline Cleaving Enzyme, BIOCHEM BIOPHYS ACTA 569, 184 (1979; and a peptide substrate for plasmin by Pierzchala, A New Fluorogenic Substrate for Plasmin, Biochem J. 183, 555 (1979).

Example 7

PREPARATION OF A SUBSTRATE HAVING AN OCTANOYL ESTER BLOCKING GROUP AT THE 7-POSITION AND A CHLOROMETHYL GROUP AT THE 4-POSITION OF COUMARIN

The following compound is prepared:

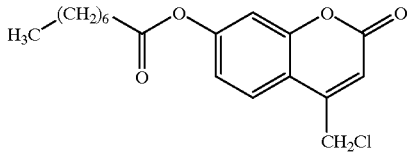

Preparation of 7-octanoyloxy-4-chloromethylcoumarin:

7-Hydroxy-4-chloromethyl coumarin (0.210 g, 1.0 mmole) is dissolved in dry dimethylformamide (3 mL) containing octanoyl chloride (0.163 g, 1.0 mmoles). To this mixture is added a catalytic quantity of diisopropylethylamine. After stirring at ambient temperature for 17 hours, the reaction is quenched with water 10 mL. This mixture is extracted with chloroform (2×10 mL). The organic layer is dried over anhydrous sodium sulfate, filtered, and the solvent is removed in-vacuo. The product residue is purified by chromatography (5×17 cm column of 35–70 $\mu$m silica gel G), and eluted with chloroform. Fractions containing product are combined, evaporated and dried in-vacuo. The non-fluorescent residue is collected after crystallization from methanol:diethyl ether (1:5).

Example 8

PREPARATION OF A SUBSTRATE HAVING A METHYL ETHER BLOCKING GROUP AT THE 7-POSITION AND A CHLOROMETHYL GROUP AT THE 4-POSITION OF COUMARIN

The following compound is prepared:

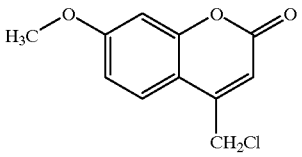

Preparation of 7-methoxy-4-chloromethylcoumarin:

To a mixture of 3-methoxyphenol (1.24 g, 10.0 mmoles) and ethyl 4-chloroacetoacetate (1.65 g, 10.0 mmoles) is added 0.56 mL (10.1 mmole) concentrated $H_2SO_4$. The reaction mixture spontaneously forms a waxy solid. To this is added 25 mL $H_2O$. The solid is broken up, heated to 100° C., and allowed to cool. The solid is separated by filtration. The product is recrystallized from 2:1 ethanol:chloroform. The crystals are filtered and washed with $H_2O$ (1.33 g, yield: 59%).

Example 9

PREPARATION OF A PEPTIDASE SUBSTRATE HAVING A p-CHLOROMETHYLBENZOYL GROUP ON THE 6'-POSITION AND LEUCINE ON THE Y-AMINO POSITION OF RHODAMINE 110

The following compound is prepared:

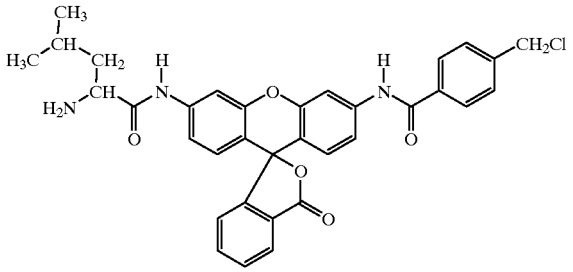

Preparation of (t-BOC-L-leucine)-rhodamine 110:

To a solution of L-leucine with a t-BOC protected amino group (0.68 g, 5.45 mmol) in 100 mL dry 1:1 pyridine:DMF at 0° C. is added 0.52 g 1-ethyl-3-(3-dimethylaminopropyl) carbodiimide, hydrochloride (EDAC, 2.73 mmol) in one portion. The mixture is stirred at 0°–5° C. for 15 minutes, and 2 g rhodamine 110 (5.45 mmol) is added in one portion. The resulting mixture is allowed to warm to room temperature and stirred for 2 days. Solvent is removed from the reaction mixture under vacuum, and the residue is purified using column chromatography (silica gel, 3% MeOH in $CHCl_3$). Yield of the t-BOC-leucine conjugate is 1.15 g.

Preparation of (t-BOC-L-leucine)-rhodamine 110-p-chloromethylbenzamide:

To a solution of the 1.15 g t-BOC-L-leucine conjugate prepared above (2.12 mmol) and diisopropylethylamine (0.56 mL, 3.17 mmol) in 20 mL $CHCl_3$ at 0° C. is added dropwise a solution of p-chloromethylbenzoyl chloride (0.5 g, 2.54 mmol) in 10 mL $CHCl_3$. The solution is allowed to warm to room temperature and then stirred overnight. Solvent is removed from the solution under vacuum and the residue is purified using column chromatography (silica gel, 10:0.1 $CHCl_3$/MeOH). The resulting crude product is purified again using column chromatography (silica gel, 7:3 ethyl acetate: hexanes). Yield of t-BOC-L-leucine-rhodamine 110-p-chloromethylbenzamide is 0.15 g.

Preparation of L-leucine-rhodamine 110-p-chloromethylbenzamide:

To a solution of the previously t-BOC-L-leucine-rhodamine 110-p-chloromethylbenzamide (0.15 g, 0.22 mmol) in MeOH at 0° C. is added 2 mL trifluoroacetic acid. The solution is stirred at 0° C. for 15 minutes, then solvent is removed under vacuum. The residue is redissolved in 2 mL MeOH to which 2 drops of concentrated HCl has been added. The resulting solution is added dropwise to 50 mL vigorously stirred diethyl ether. The resulting precipitate is collected by centrifugation and dried under vacuum overnight. The yield of the L-leucine-rhodamine 110-p-chloromethylbenzamide complex is 0.1 g. (mp 275° C., dec).

Variation in spacers:

L-leucine-rhodamine 110-p-chloromethylbenzenesulfonamide is prepared by reacting the rhodamine 110 with p-chloromethylbenzenesulfonyl chloride in place of p-chloromethylbenzoyl chloride. Similar substrates having a carbonyl spacer or sulfonyl spacer are prepared using chloroacetyl chloride and chloromethylsulfonyl chloride, respectively, in the presence of a suitable base.

Example 10

PREPARATION OF A PEPTIDASE SUBSTRATE HAVING A p-CHLOROMETHYLBENZENESULFONAMIDE GROUP AT THE 3'-HYDROXYL AND L-LEUCINE ON THE 6'-AMINE OF RHODOL

The following compound is prepared:

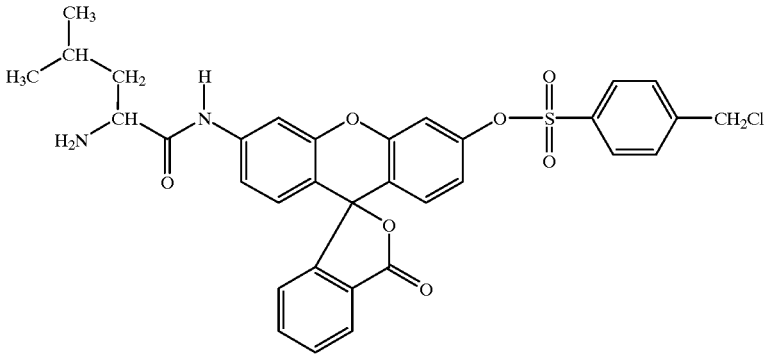

Preparation of N-(t-BOC-leucine)-rhodol:

To a 50 mL round bottom flask cooled in an ice/water bath is added 15 mL dry DMF/pyridine (1:1 v/v). The solution is stirred for 10 minutes, followed by the addition of 1.0 g (4.3 mmol) of N-t-BOC-L-leucine and 0.83 g (4.3 mmol) of 1-ethyl-3-(3-dimethylaminopropyl) carbodiimide (EDAC). After 10–15 min of stirring, 1.4 g (4.3 mmol) of rhodol dissolved in 15 mL pyridine/DMF is added. After stirring for two hours in ice bath, the solution is warmed to room temperature and stirred an additional two days. The solvent is removed under high vacuum at room temperature. The residue is purified using column chromatography (silica gel, MeOH/$CHCl_3$) and characterized by thin layer chromatography and $^1H$ NMR spectroscopy.

Preparation of p-chloromethylbenzenesulfonyl chloride:

To a 250 mL flask, fitted with addition funnel, reflux condenser and thermometer, is placed 50 g (0.43 mole) of chlorosulfonic acid. Benzyl chloride, (18 g, 0.14 mole) is added to the reaction mixture, slowly, with continuous stirring, over a period of two hours. The temperature of the reaction is kept near room temperature using a water bath. After the addition is complete, the stirring is continued for at least one hour. After analysis by thin layer chromatography shows that the reaction is complete, the reaction mixture is poured into 150 g of crushed ice. The solid is collected and washed with cold water several times. The crude product is further purified by recrystallization. The product is characterized using $^1$H NMR spectroscopy.

Preparation of N-(t-BOC-leucine)-rhodol-p-chloromethylbenzenesulfonyl ester:

To a stirred solution of N-(t-BOC-L-leucin)-rhodol (1.0 g, 18 mmol) and triethylamine (0.2 g, 2.0 mmol) in 15 mL dry DMF cooled in a ice bath is added dropwise 0.61 g (2.7 mmol) of p-chloromethylbenzenesulfonyl chloride in 5 mL dry DMF. The solution is stirred under nitrogen for two hours in an ice bath and then two days at room temperature. The solvent is removed under high vacuum at room temperature. The crude product is purified using column chromatography (silica gel, MeOH/$CHCl_3$). The product is characterized using $^1$H NMR spectroscopy.

Preparation of N-leucine-rhodol-p-chloromethylbenzenesulfonyl ester:

The protected substrate is deprotected using a procedure exactly analogous to that described in Example 9.

Variation in spacers:

N-(p-Chloromethylbenzoyl)-rhodol: To a stirred cold solution of rhodol (1.0 g, 3.0 mmol) and triethylamine (0.37 g, 3.6 mmoles) in 15 mL dry DMF in an ice bath is added p-chloromethylbenzoic acid chloride (0.57 g, 3.0 mmol) in 5 mL dry DMF dropwise over ½ hr. The solution is stirred in the ice bath for 2 hours, and then warmed to room temperature and stirred an additional 24 hrs. The solvent is removed at room temperature under high vacuum. The crude product is purified using column chromatography. The product is characterized using $^1$H NMR spectroscopy.

N-(p-Chloromethylbenzenesulfonyl-rhodol: This product is prepared exactly analogously to N-(p-chloromethylbenzoyl)rhodol (above) except using p-chloromethylbenzenesulfonyl chloride in place of p-chloromethylbenzoyl chloride.

Preparation of other enzyme substrates:

Similar reporter molecules, including the glycosides and phosphates, are prepared by treating the desired XR-rhodol intermediate (as prepared above) with the desired BLOCK precursors, for example those described for fluorescein in Examples 1 and 5.

Example 11

THE PRODUCTS FROM A NEW GALACTOSIDASE SUBSTRATE, 4-CHLOROMETHYLUMBELLIFERYL β-D-GALACTOSIDE (Cl-MUG) ARE WELL RETAINED IN A LACZ POSITIVE CELLS BEFORE AND AFTER FIXATION

1. Fibroblast Cell Line and Staining Procedure:

1.1. Cell Lines:

NIH/3T3 cells (lacZ negative) and CRE BAG 2 cells (3T3 cells transformed with a retrovirus containing lacZ gene) are employed for cellular assays. Both cell lines can be obtained from American Type Culture Collection Co., Rockville, Md. The cells are grown in a humidified atmosphere of 5% $CO_2$ in Dulbecco's modified Eagle's medium supplemented with 10% calf serum, 50 μg/mL gentamicin, 300 μg/mL L-glutamine and 10 mM HEPES pH 7.4.

1.2. Stock Solution of Labeling Reagent:

4-Chloromethylumbelliferyl β-D-galactoside (Cl-MUG) (Example 3) is dissolved in DMSO to get a 10 mM stock solution. A 10 mM stock solution of 4-methylumbelliferyl β-D-galactoside (MUG) (Molecular Probes) is also made in DMSO as a control. The stock solutions are kept sealed in brown reagent bottles and stored at −20° C.

1.3. Working Medium:

100 μL of stock solution is added to 10 mL of fresh culture medium to prepare a "working medium" containing 100 μM Cl-MUG. This medium is filter-sterilized by passing through an Acrodisc™ filter (0.45 μm pore size). A working medium containing MUG is prepared in the same way.

1.4. Staining of Cells:

Cells grown on coverslips are transferred to the working medium and incubated at 37° C. under normal conditions. Cells are examined at the desired time for their fluorescence under a Zeiss microscope equipped with a Hoechst filter set (EX 365 um/EM 480 nm). After incubation for 60 minutes, followed by washing with fresh medium, fluorescence is observed in the cytoplasmic area of the lacZ positive CRE BAG 2 cells, but not in 3T3 cells. After 6 hours continuous incubation, the fluorescence intensity of stained CRE BAG 2 cells reaches its highest level.

1.5. Cytoxicity:

This substrate shows no cytotoxicity to either type of cell. Cells incubated in 100 μM Cl-MUG working medium for 24 hours look morphologically normal and have the same population doubling time as the cells incubated in substrate-free medium. Cells preincubated in the working medium for 6 hours can be subcultured and incubated in fresh medium resulting in the formation of a second generation of cells that is normal. Fluorescence can be detected in the cells for at least 24 hours following washing of the cells with fresh medium.

2. Cell Fixation and Dye Retention:

2.1. Fixation of Stained Cells:

The cells grown on coverslips and incubated with either Cl-MUG or MUG are immersed in 3.7% paraformaldehyde in 80 mM Pipes buffer, pH 6.5 for 4 minutes to allow the paraformaldehyde to penetrate the cells. The cells are then transferred to 3.7% paraformaldehyde in PBS. After 6 minutes, the cells are washed three times with PBS buffer for ten minutes. The coverslips are put on the slides and sealed.

2.2. Dye Retention:

The fixed cells are examined for their fluorescence under a Zeiss microscope equipped with a Hoechst filter set. The cells stained with Cl-MUG are still brightly fluorescent while those stained with MUG are barely fluorescent. This indicates that the fluorescent products, enzymatically cleaved from Cl-MUG, react with intracellular thiols and form cell-impermeant fluorescent adducts, which improves the dye retention after cell fixation.

Example 12

LABELING OF LACZ POSITIVE CELLS WITH CHLOROMETHYLFLUORESCEIN DI-β-D-GALACTOSIDE (CMFDG) USING HYPOOSMOTIC SHOCK

Cell Lines:

The same cell lines as used in Example 11 are used for these experiments.

2. Stock Solutions of Labeling Reagents:

5-Chloromethylfluorescein di-β-D-galactoside (CMFDG) (Example 1) is dissolved in DMSO to get 20 mM stock solution. A 40 mM stock solution offluorescein di-β-D-galaetoside (FDG) (Molecular Probes) is also made in DMSO as a control. The stock solutions are kept sealed in brown reagent bottles and stored at −20° C.

3. FCS-PBS Solution and Staining Solution:
   (A) FCS-PBS Solution: Phosphate buffered saline (GIBCO), 4% fetal calf serum, 10 mM HEPES, pH 7.2
   (B) Staining Solution: CMFDG: 200 μL of stock solution is diluted with distilled water to 4 mL to get a 1 mM staining solution. FDG: 400 μL of stock solution is diluted to 4 mL with distilled water to get a 4 mM staining solution.
4. Staining and Examination of Cells:

Cells grown on coverslips are transferred to a Petri dish containing 3 mL of FCS-PBS solution and then incubated at 37° C. for 10 minutes. 3 mL of prewarmed (37° C.) 1 mM CMFDG staining solution is added to give a final dye concentration of 0.5 mM The solutions are mixed rapidly. The cells are incubated at 37° C. for exactly one minute. To stop the loading, the cells are transferred to a 1.8 mL of ice-cold FCS-PBS solution. FDG is loaded into cells by using the same procedure except that the final dye concentrations is 2 mM. Cells are then incubated under normal culture conditions to examine the dye retention. Cells are examined without washing at the desired time for their fluorescence under a Zeiss microscope equipped with a FITC filter set (EX 485 nm/EM 530 nm).

5. Cellular Retention:

After incubation for 10 minutes, the lacZ positive CRE BAG 2 cells loaded with 0.5 mM CMFDG are very well stained and much brighter than those loaded with 2 mM FDG. After incubation for 4 hours, more than 70% of CMFDG stained CRE BAG 2 cells are apparently as bright as after 10 minutes incubation, while the CRE BAG 2 cells stained with FDG are very dim with high background fluorescence in the medium. CMFDG shows no cytotoxicity. Cells incubated in 500 μM CMFDG staining medium for 24 hours appear morphologically normal and have the same population doubling time as the control.

Example 13

USING CHLOROMETHYLFLUORESCEIN DI-β-D-GALACTOPYRANOSIDE (CMFDG) TO MEASURE THE LEVEL OF MARKER GENE EXPRESSION

Because the CMFDG substrate generates a product that is so well retained by cells (Examples 11 and 12), it can be used for quantitative measurements of lacZ expression.

1. A series of lacZ gene containing plasmids, each with a modified yeast promoter are used. When transferred into the appropriate strains of Saccharomyces cerevisiae, each plasmid confers a different level of lacZ gene expression. Yeast strains EG123 and HR125-5d, transformed with these plasmids, are grown in special minimal medium for plasmid maintenance and, after reaching the appropriate level of growth, are assayed for lacZ gene expression as measured by β-galactosidase activity.
2. The β-galactosidase activity of one aliquot of these transformed yeast cells is measured using o-nitrophenyl-β-D-galactopyranoside (ONPG).
3. Another aliquot of yeast cells is loaded with the fluorogenic substrate CMFDG as indicated in Example 12. Following washing to remove any dye that has leaked from the cells, the fluorescence intensity of the remaining cells as measured in a CytoFluor 2300 fluorescence plate reader (Millipore) can be measured over time. Each lacZ-positive yeast strain shows a linear increase in fluorescence when plotted over time. The amount of increase over time can be calculated from the slope of the plotted increase using linear regression. Each yeast strain accumulates fluorescent product at a characteristic rate, as reflected in the differences in the slopes of the various lines.
4. The slopes of these lines can be used to calculate the β-galactosidase activity of each yeast strain. The obtained values are compared with the assays using ONPG substrate to confirm that the fluorescence intensity as measured over time correlates well with the level of lacZ expression (enzyme activity) in these transformed yeast cells. Intensity measurements in single cells by flow cytometry using FDG have been extensively described by Nolan et al. [Nolan G. P., Fiering, S., Nicolas, J. F., Herzenberg, L. A., PROC. NATL. ACAD. SCI. USA 85, 2603 (1988] that can be improved by use of CMFDG, which is shown in Example 12 to give a product that is better retained than that formed from FDG and to be useable under physiological conditions of incubation. Certain products such as 4-chloromethylumbelliferyl β-D-galactoside (Cl-MUG) can be loaded into living cells without requiring hypotonic shock (see Example 11).

Example 14

MEASUREMENT OF GLUTATHIONE TRANSFERASE ACTIVITY USING CHLOROMETHYLFLUORESCEIN AS SUBSTRATE

Activity of glutathione transferase in vitro can be assayed essentially by the method of Grants and Matsumura (INSECT PHYSIOL. 18 (6), 615 (1988)).

1) Reagents: The stock reagents required are: 1) 5-Chloromethylfluorescein (CMF) substrate (Example 1) 10 mg/mL in DMF, diluted 1:10 in reaction buffer to 1 mg/mL; 2). Reaction buffer 100 mM potassium phosphate, 15% glycerol pH 6.8; 3). Glutathione (GSH) 155 mM in 20 mM TRIS, 2 mM DTT, 15% glycerol pH 7.8; 4). Glutathione Transferase from Equine Liver (Sigma #G 6511) 1.0 mg/mL in reaction buffer.
2) Assay. The reaction mixture consists of 0.7 mL reaction buffer, 0.1 mL GSH, 0.1 mL substrate and 0.1 mL enzyme. The background is measured and subtracted by using 0.1 mL of the reaction buffer instead of the enzyme. Enzymatic activity can be detected at less than 5 minutes at room temperature. Product formation can be detected by separation of the polar product from the less polar substrate by a suitable means such as thin layer chromatography or high performance liquid chromatography. For instance, product accumulation can be detected by thin layer chromatography using A) 15:85 methanol:chloroform or B) 2:5:15 $NH_4OH$:isopropyl alcohol:methanol. In system A the product does not move from the origin whereas the substrate has an intermediate mobility relative to the solvent front. In system B the product moves from the origin, with an $R_f$ identical to that of an authentic standard for the glutathione adduct of chloromethyl fluorescein prepared by a nonenzyme catalyzed reaction, whereas the substrate moves with the solvent front. For quantitative measurement the products are scraped from the plate, dissolved in 1% aqueous ammonium hydroxide and the absorbance at 492 nm determined using an extinction coefficient of 75,000 $cm^{-1}M^{-1}$ for fluorescein. Alternatively the fluorescence of the product is determined using a fluorometer versus a fluorescein standard with excitation at 492 and emission measured at 515 nm.

Product accumulation can be quantitated by the following procedure: 1 mL of the reaction mixture is extracted with 2 mL of ethyl acetate and the pH is adjusted to about 4 (3.5–4.3) with 1M HCl (~20 μL). The aqueous layer is separated using a modified transfer pipette as a miniature separatory funnel and the absorbance or fluorescence is determined as above.

Example 15

MEASUREMENT OF CYTOTOXICITY USING CHLOROMETHYLFLUORESCEIN DI β-D-GALACTOPYRANOSIDE AND 7-(β-D-GALACTOPYRANOSYLOXY)-4-CHLOROMETHYLCOUMARIN

1) Reagents 5-Chloromethylfluorescein di-β-D-galactopyranoside (CMFDG) (Example 1) and 7-(β-D-galactopyranosyloxy)-4-chloromethylcoumarin (Cl-MUG) (Example 3) are separately dissolved at 10 mM anhydrous DMSO and stored frozen at −20° C. until needed. Saponin is dissolved in PBS at a concentration of 0.04%.

2) Cell Lines:

NIH/3T3 cells (lacZ negative) and CRE BAG 2 cells (3T3 cells transformed with a retrovirus containing latZ gene) are employed for cellular assays. Both cell lines can be obtained from American Type Culture Collection Co., Rockville, Md. The cells are grown in a humidified atmosphere of 5% $CO_2$ in Dulbecco's modified Eagle's medium supplemented with 10% calf serum, 50 μg/mL gentamicin, 300 μg/mL L-glutamine and 10 mM HEPES pH7.4.

3) Assay using CMFDG:

The experiment is most conveniently performed in a CytoFluor™ 2300 fluorescence plate reader (Millipore) but can be performed qualitatively on a microscope slide or quantitatively in a flow cytometery, or in any system that permits washing of the cells following addition of the cytotoxic agent. 200 μL of NIH 3T3 cells are transferred to several wells of a sterilized 96 well plate and permitted to recover and attach for 1 hour. The cells are loaded with 10 μM CMFDG for 30 minutes at 37° C. The brightly fluorescent cells are washed with fresh medium then reconstituted to 200 μL total volume. Fluorescence of each well is determined using a 485 nm excitation filter, a 530 nm emission filter and sensitivity setting 1. To each well is added saponin as a lysing agent in concentrations varying from 0 to 0.004%. Following an incubation of approximately 15 minutes the wells are washed with fresh medium, reconstituted to 200 μL with fresh medium and remeasured as above. Loss of fluorescence from the sample is correlated with the loss of integrity of the membrane and thus the cytotoxicity of the reagent. Using the above conditions it is found that 50% of the signal is lost when the cells are incubated with about 0.001% saponin while greater than 90% signal loss is observed using a 0.02% solution.

4) Assay using Cl-MUG.

The CRE BAG 2 cells are loaded with Cl-MUG as described in Example 11. The assay of viability of the lacZ transfected cells is conducted essentially as described immediately above for the assay of NIH 3T3 cells using CMFDG. The results of the saponin cytotoxicity measurement using the two reagents are comparable for the two reagents.

Example 16

COMPARISON OF CELLULAR RETENTION OF A CHLOROMETHYL-SUBSTITUTED AND NON-SUBSTITUTED RHODAMINE 110 PEPTIDASE SUBSTRATES

1) Cell Lines:

NIH/3T3 cells are prepared as described in Example 15.

Staining solutions of bis-(L-leucine)-rhodamine 110 and L-leucine-rhodamine 110-p-chloromethylbenzamide (Example 9), respectively, are prepared that are 25 μM in concentration. Equivalent NIH/3T3 cells are incubated with the same amount of peptidase substrate for thirty (30) minutes at 37° C. in Modified Tyrode's buffered saline (135 mM NaCl, 5 mM KCl, 1 mM $MgCl_2$, 1.8 mM $CaCl_2$, 10 mM NaHEPES, 5.6 mM glucose, pH 7.5, plus 0.1% bovine serum albumin).

[Adler] *After* staining, the cells stained with the bis-L-leucine substrate exhibit substantial leakage of the rhodamine 110 enzyme reaction product, while the cells stained with the chloromethyl-substituted Rhodamine 110 substrate show significantly less leakage. The cells are washed and placed in fresh media for several hours. The cells stained with bis-(L-leucine)-rhodamine 110 show no fluorescent signal upon illumination, while the L-leucine-Rhodamine 110-p-chloromethylbenzamide stained cells show a bright, well-defined staining pattern when viewed using a fluorescein long-pass filter set.

Example 17

COMPARISON OF CELLULAR RETENTION OF CHLOROMETHYL-SUBSTITUTED SUBSTRATE VS. THE ANALOGOUS METHYL- AND TRIFLUOROMETHYL-SUBSTITUTED SUBSTRATES

CRE-BAG2 cells are prepared as described in Example 15.

Staining solutions of 4-methylcoumarin β-D-galactopyranoside, 4-chloromethylcoumarin β-D-galactopyranoside and 4-trifluoromethylcoumarin β-D-galactopyranoside, respectively, are prepared that are 10 μM in concentration. Each galactopyranoside substrate is loaded into CRE-BAG2 cells expressing β-galactosidase using brief hypotonic shock for less than five minutes. Cells are then washed free of extracellular substrate and incubated for three hours in fresh culture medium at 37° C. Each cell sample is then illuminated at 360±20 nm, and the fluorescence is observed at >400 nm. Fluorescence intensity data is acquired using a cooled CCD camera and subsequently stored in digital format. The cell samples incubated with the methylcoumarin and trifluoromethylcoumarin substrates show low fluorescent intensity, while the cells incubated with the galactosidase substrate having a choromethyl substituent are brightly fluorescent.

It is to be understood that, while the foregoing invention has been described in detail by way of illustration and example, numerous modifications, substitutions, and alterations are possible without departing from the spirit and scope of the invention as described in the following claims.

What is claimed is:

1. A substrate having the formula:

XR-SPACER-REPORTER-BLOCK wherein BLOCK is a monovalent moiety derived by removal of a hydroxy group from phosphate or from sulfate, or biologically compatible salt thereof; or a monovalent moiety derived by removal of a hydroxy group from a carboxy group of an aromatic carboxylic acid or of an amino acid, protected amino acid, peptide, or protected peptide; or a monovalent moiety derived by removal of a hydroxy group from an alcohol or from a mono- or polysaccharide, where said BLOCK is selected to be removable from -REPORTER by action of an enzyme; -REPORTER- is an anthracene, a benzphenalenone, an acridinone [, a coumarin], a fluorescein, a naphthalene, a phenalenone, a pyrene, a resorufin, a rhodol, or a rhodamine, that when no longer bound to BLOCK by a BLOCK-REPORTER bond, is fluorescent; -SPACER- is a single covalent bond, or a covalent linkage having 0–8 carbon atoms and 1–4 heteroatoms, wherein said heteroatoms, which may be the same or different, are selected from the group consisting of O, N and S; and XR— is a haloalkyl moiety, where X is a single Cl, I, or Br, and R is an alkyl linkage having 1–4 carbons.

2. A substrate, as claimed in claim 1, wherein -SPACER-XR is one of —(C═O)—XR, —($SO_2$)—XR, XR—$C_6H_4$—(C═O)—, or XR—$C_6H_4$—($SO_2$)—.

3. A substrate, as claimed in claim 1, wherein the BLOCK-REPORTER bond is an amide bond that results from removal of a hydroxy group from a carboxylic acid of an amino acid or peptide and a hydrogen atom from an amino moiety on REPORTER.

4. A substrate, as claimed in claim 1, wherein the BLOCK-REPORTER bond is an ether bond formed by removal of a hydroxy group from a lower alcohol having 6 or less carbon atoms or of hydroxy from a mono- or polysaccharide and a hydrogen atom from a phenolic moiety on REPORTER.

5. A substrate, as claimed in claim 1, wherein the BLOCK-REPORTER bond is an ester bond, wherein the ester is an ester of a guanidinobenzoic, phosphoric, or sulfuric acid, or a biologically compatible salt thereof.

6. A substrate, as claimed in claim 1, that is an ether of either a fluorescein or a rhodol and a lower alcohol having 6 or fewer carbon atoms, or a [steriodal] *steroidal* alcohol, or of a mono- or polysaccharide, and XR— is $XCH_2$—.

7. A substrate, as claimed in claim 6, where the monosaccharide is β-D-galactose, β-D-glucose or β-D-glucuronic acid and XR— is $ClCH_2$—.

8. A substrate, as claimed in claim [1] *25*, that is an ether of a 7-hydroxycoumarin and a mono- or polysaccharide, or a lower alcohol having [6 or fewer] *2–6* carbon atoms, or a steroidal alcohol, and XR- is $XCH_2$—.

9. A substrate, as claimed in claim 8, where the monosaccharide is β-D-galactose, β-D-glucose or β-D-glucuronic acid and XR— is $ClCH_2$—.

10. A substrate, as claimed in claim 1, that is an ether of a fluorescein and a mono- or polysaccharide, or a lower alcohol having 6 or fewer carbon atoms, and XR— is $XCH_2$—.

11. A substrate, as claimed in claim 10, where the monosaccharide is β-D-galactose, β-D-glucose or β-D-glucuronic acid and XR— is $CHCl_2$—.

12. A substrate, as claimed in claim 1, that is an amide of a 7-aminocoumarin and an amino acid or peptide or a biologically compatible salt of an amino acid or peptide and XR— is $XCH_2$—.

13. A substrate, as claimed in claim 1, that is an amide of rhodamine 110 and an amino acid, protected amino acid, or peptide, or a biologically compatible salt of an amino acid or peptide, and XR— is $XCH_2$—.

14. A substrate, as claimed in claim 1, that is an amide of rhodamine 110 and an amino acid, protected ammo acid or peptide or biologically compatible salt of an amino acid, protected amino acid or peptide, and -SPACER- is a carboxamide or sulfonamide bound to the second rhodamine nitrogen.

15. A substrate, as claimed in claim 1, having the formula

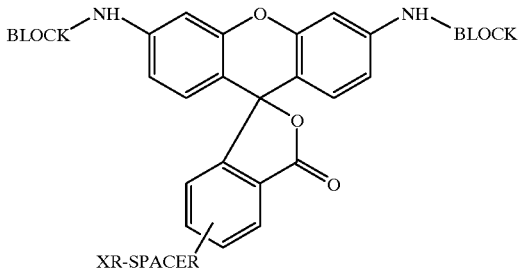

16. A substrate, as claimed in claim 1, having the formula

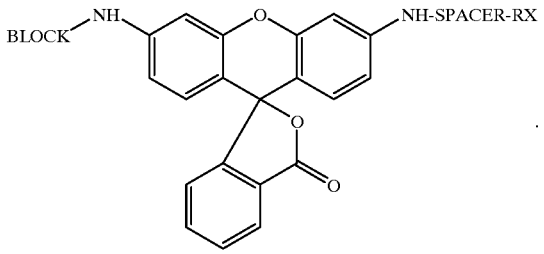

17. A substrate, as claimed in claim 16, wherein XR-SPACER- is one of XR—(C═O)—, XR—($SO_2$)—, XR—$C_6H_4$—(C═O), or XR—$C_6H_4$—($SO_2$)—.

18. A substrate, as claimed in claim 1, having the formula

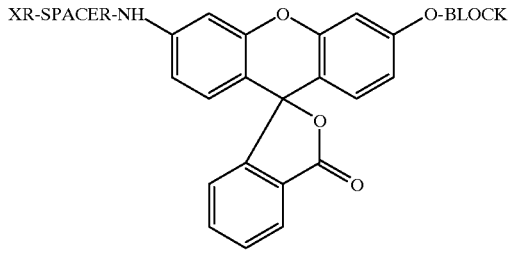

19. A substrate, as claimed in claim 1, having the formula

[

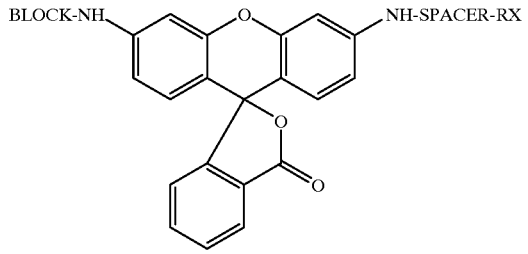

]

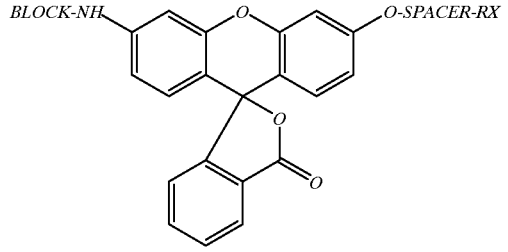

20. A substrate, as claimed in claim [1] *25*, having the formula

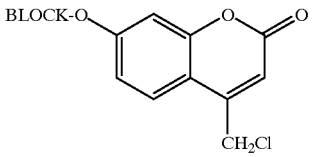

21. A substrate, as claimed in claim [1] *25*, having the formula

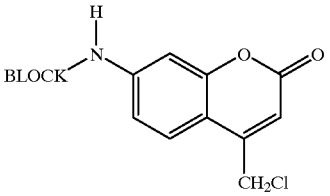

22. A fluorescent enzymatic reaction [producing] *product having* the formula

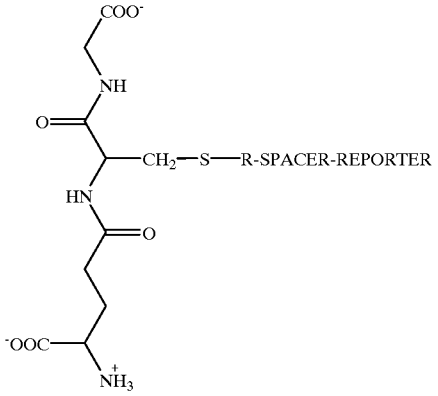

where REPORTER is an anthracene, a benzphenalenone, an acridinone, a coumarin, a fluorescein, a naphthalene, phenalenone, a pyrene, a resorufin, a rhodol, or a rhodamine;

-SPACER- is a single covalent bond, or a covalent linkage having 0–8 carbon atoms and 1–4 heteroatoms, wherein said heteroatoms, which may be the same or different, are selected from the group consisting of O, N and S; and R is an alkyl linker having 1–4 carbon atoms;

wherein, in the presence of reduced glutathione, said enzymatic reaction product is the result of the action of an analyte enzyme on the substrate

XR-SPACER-REPORTER-BLOCK wherein BLOCK is a monovalent moiety derived by removal of a hydroxy group from phosphate or from sulfate, or a biologically compatible salt thereof; or a monovalent moiety derived by removal of a hydroxy group from a carboxy group of an aromatic carboxylic acid or of an amino acid or of a peptide; or a monovalent moiety derived by removal of a hydroxy group from an alcohol or from a mono- or polysaccharide, where said BLOCK is selected to be removable from -REPORTER by action of an analyte enzyme; and X is a single Cl, I, or Br.

23. A fluorescent enzymatic reaction product, as claimed in claim 22, wherein said analyte enzyme is present intracellularly.

24. A fluorescent enzymatic reaction product, as claimed in claim 22, where REPORTER is a coumarin, a fluorescein, a resorufin, a rhodol, or a rhodamine.

*25. A substrate having the formula:*

*XR-SPACER-REPORTER-BLOCK*

*wherein BLOCK is a monovalent moiety derived by removal of a hydroxy group from phosphate or from sulfate, or a biologically compatible salt thereof; or a monovalent moiety derived by removal of a hydroxy group from a carboxy group of an aromatic carboxylic acid or of an amino acid, protected amino acid, peptide, or protected peptide; or a monovalent moiety derived by removal of a hydroxy group from an alcohol having 2–6 carbons, or from a steroidal alcohol, or from a mono- or polysaccharide, where said BLOCK is selected to be removable from -REPORTER by*

*action of an enzyme; -REPORTER- is a coumarin, that when no longer bound to BLOCK by a BLOCK-REPORTER bond, is fluorescent; -SPACER- is a single covalent bond, or a covalent linkage having 0–8 carbon atoms and 1–4 heteroatoms, wherein said heteroatoms, which may be the same or different, are selected from the group consisting of O, N and S; and XR— is a haloalkyl moiety, where X is a single Cl, I, or Br, and R is an alkyl linkage having 1–4 carbons.*

* * * * *